United States Patent
Chackalamannil et al.

(10) Patent No.: US 6,645,987 B2
(45) Date of Patent: Nov. 11, 2003

(54) NOR-SECO HIMBACINE DERIVATIVES USEFUL AS THROMBIN RECEPTOR ANTAGONISTS

(75) Inventors: Samuel Chackalamannil, East Brunswick, NJ (US); Mariappan V. Chelliah, Edison, NJ (US); Yan Xia, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 53 days.

(21) Appl. No.: 09/880,222

(22) Filed: Jun. 13, 2001

(65) Prior Publication Data

US 2002/0026050 A1 Feb. 28, 2002

Related U.S. Application Data

(60) Provisional application No. 60/211,724, filed on Jun. 15, 2000.

(51) Int. Cl.[7] ............... A61K 31/443; C07D 405/06
(52) U.S. Cl. ............ 514/337; 546/284.1; 546/284.7
(58) Field of Search ............... 546/284.1, 284.7; 514/337

(56) References Cited

U.S. PATENT DOCUMENTS

| | | | | |
|---|---|---|---|---|
| 6,063,847 | A | * 5/2000 | Chackalamannil et al. | . 524/297 |
| 6,326,380 | B1 | * 12/2001 | Chackalamannil et al. | . 514/311 |

FOREIGN PATENT DOCUMENTS

| | | |
|---|---|---|
| WO | 94/03479 | 2/1994 |
| WO | 9926943 | * 6/1999 |

OTHER PUBLICATIONS

Bernatowicz et al, *J. Med. Chem.*, 39 (1996), p. 4879–4887.
Chackalamannil et al, *J. Am. Chem. Soc.*, 118 (1996), p. 9812–9813.
Pertwee, *Curr. Med. Chem.*, 6 (1999), p. 635–664.
Mordini et al, *J. Org. Chem.*, 59 (1994), p. 4784–4790.
McGinnis et al, *J. Chem. Soc.*, (1941), p. 404–408.
Wang et al, *Tet. Lett.*, 41 (2000), p. 4335–4338.
Natarajan et al, *Int. J. Peptide Protein Res.*, 45 (1995), p. 145–151.
Lowrey et al, *J. Biol. Chem.*, 193 (1951), 265–275.
Ahn et al, *Mol. Pharmacol.*, 51 (1997), p. 350–356.
Bednar et al, *Thromb. Res.*, 77 (1995), p. 453–463.
Even–Ram et al, *Nature Med.*, 4, (8) (1988), p. 909–914.
Showalter et al, *J. Pharmacol. Exp. Ther.*, 278 (3) (1996), p. 989–999.

\* cited by examiner

*Primary Examiner*—Rita Desai
(74) *Attorney, Agent, or Firm*—Anita W. Magatti

(57) ABSTRACT

Heterocyclic-substituted compounds of the formula

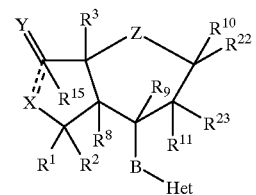

or a pharmaceutically acceptable salt thereof, are disclosed.

14 Claims, No Drawings

NOR-SECO HIMBACINE DERIVATIVES USEFUL AS THROMBIN RECEPTOR ANTAGONISTS

CROSS REFERENCE TO RELATED APPLICATION

This application claims the benefit of U.S. Provisional Application Serial No. 60/211,724, filed Jun. 15, 2000.

BACKGROUND OF THE INVENTION

The present invention relates to nor-seco himbacine derivatives useful as thrombin receptor antagonists in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor (PAR) antagonists. The compounds of the invention also bind to cannabinoid (CB2) receptors and are useful in the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis. The invention also relates to pharmaceutical compositions containing said compounds.

Thrombin is known to have a variety of activities in different cell types and thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, 39 (1996), p. 4879–4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor anatgonists are also disclosed in WO 94/03479, published Feb. 17, 1994.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, a selective $CB_2$ receptor binding agent is expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, *Curr. Med. Chem.* 6(8), (1999), 635).

Himbacine, a piperidine alkaloid of the formula

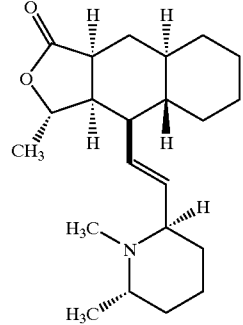

has been identified as a muscarinic receptor antagonist. The total synthesis of (+)-himbacine is disclosed in Chackalamannil et al, *J. Am. Chem. Soc.*, 118 (1996), p. 9812–9813.

Tricyclic himbacine-related compounds have been disclosed as thrombin receptor antagonists in U.S. Pat. No. 6,063,847.

SUMMARY OF THE INVENTION

The present invention relates to thrombin receptor antagonists represented by the formula I

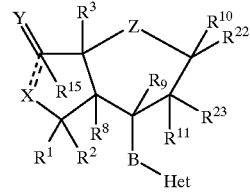

or a pharmaceutically acceptable salt thereof, wherein:
Z is $-(CH_2)_n-$;

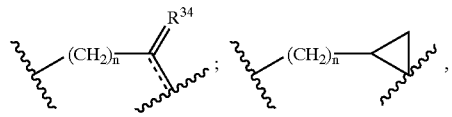

wherein $R^{10}$ is absent; or

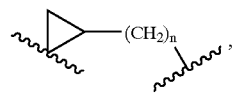

wherein $R^3$ is absent;
the single dotted line represents an optional double bond;
the double dotted line represents an optional single bond;
n is 0–2;
$R^1$ and $R^2$ are independently selected from the group consisting of H, $C_1$–$C_6$ alkyl, fluoro($C_1$–$C_6$)alkyl, difluoro($C_1$–$C_6$)alkyl, trifluoro-($C_1$–$C_6$)alkyl, $C_3$–$C_7$ cycloalkyl, $C_2$–$C_6$ alkenyl, aryl($C_1$–$C_6$)alkyl, aryl ($C_2$–$C_6$)alkenyl, heteroaryl($C_1$–$C_6$)alkyl, heteroaryl ($C_2$–$C_6$)alkenyl, hydroxy-($C_1$–$C_6$)alkyl, ($C_1$–$C_6$) alkoxy($C_1$–$C_6$)alkyl, amino-($C_1$–$C_6$)alkyl, aryl and thio ($C_1$–$C_6$)alkyl; or $R^1$ and $R^2$ together form a =O group;
$R^3$ is H, hydroxy, $C_1$–$C_6$ alkoxy, $-NR^{18}R^{19}$, $-SOR^{16}$, $-SO_2R^{17}$, $-C(O)OR^{17}$, $-C(O)NR^{18}R^{19}$, $C_1$–$C_6$ alkyl, halogen, fluoro($C_1$–$C_6$)alkyl, difluoro($C_1$–$C_6$) alkyl, trifluoro($C_1$–$C_6$)alkyl, $C_3$–$C_7$ cycloalkyl, $C_2$–$C_6$ alkenyl, aryl($C_1$–$C_6$)alkyl, aryl($C_2$–$C_6$)alkenyl, heteroaryl($C_1$–$C_6$)alkyl, heteroaryl($C_2$–$C_6$)alkenyl, hydroxy($C_1$–$C_6$)alkyl, amino($C_1$–$C_6$)alkyl, aryl, thio ($C_1$–$C_6$)alkyl, ($C_1$–$C_6$)alkoxy($C_1$–$C_6$)alkyl or ($C_1$–$C_6$) alkylamino($C_1$–$C_6$)alkyl;
$R^{34}$ is (H, $R^3$), (H, $R^{43}$), =O or =$NOR^{17}$ when the optional double bond is absent; $R^{34}$ is $R^{44}$ when the double bond is present;
Het is a mono-, bi- or tricyclic heteroaromatic group of 5 to 14 atoms comprised of 1 to 13 carbon atoms and 1 to 4 heteroatoms independently selected from the group consisting of N, O and S, wherein a ring nitrogen can form an N-oxide or a quaternary group with a $C_1$–$C_4$ alkyl group, wherein Het is attached to B by a carbon atom ring member, and wherein the Het group is substituted by 1 to 4 substituents, W, independently selected from the group consisting of H; $C_1$–$C_6$ alkyl; fluoro($C_1$–$C_6$)alkyl; difluoro($C_1$–$C_6$)alkyl; trifluoro-($C_1$–$C_6$)-alkyl; $C_3$–$C_7$ cycloalkyl; heterocycloalkyl; heterocycloalkyl substituted by $C_1$–$C_6$ alkyl, $C_2$–$C_6$ alkenyl, OH—(C$_1$–C$_6$)alkyl, or =O; C$_2$–C$_6$ alkenyl; R$^{21}$-aryl(C$_1$–C$_6$)alkyl; R$^{21}$-aryl-(C$_2$–C$_6$)-alkenyl; R$^{21}$-aryloxy; R$^{21}$-aryl-NH—; heteroaryl(C$_1$–C$_6$)alkyl; heteroaryl(C$_2$–C$_6$)-alkenyl; heteroaryloxy; heteroaryl-NH—; hydroxy(C$_1$–C$_6$)alkyl; dihydroxy(C$_1$–C6)alkyl; amino(C$_1$–C$_6$)alkyl; (C$_1$–C$_6$)alkylamino-(C$_1$–C$_6$)alkyl; di-((C$_1$–C$_6$)alkyl)-amino(C$_1$–C$_6$)alkyl; thio(C$_1$–C$_6$) alkyl; C$_1$–C$_6$ alkoxy; C$_2$–C$_6$ alkenyloxy; halogen; —NR$^4$R$^5$; —CN; —OH; —COOR$^{17}$; —COR$^{16}$; —OSO$_2$CF$_3$; —CH$_2$OCH$_2$CF$_3$; (C$_1$–C$_6$)alkylthio; —C(O)NR$^4$R$^5$; —OCHR$^6$-phenyl; phenoxy-(C$_1$–C$_6$) alkyl; —NHCOR$^{16}$; —NHSO$_2$R$^{16}$; biphenyl; —OC(R$^6$)$_2$COOR$^7$; —OC(R$^6$)$_2$C(O)NR$^4$R$^5$; (C$_1$–C$_6$)alkoxy; —C(=NOR$^{17}$)R$^{18}$; C$_1$–C$_6$ alkoxy substituted by (C$_1$–C$_6$)alkyl, amino, —OH, COOR$^{17}$, —NHCOOR$^{17}$, —CONR$^4$R$^5$, aryl, aryl substituted by 1 to 3 substutuents independently selected from the group consisting of halogen, —CF$_3$, C$_1$–C$_6$ alkyl, C$_1$–C$_6$ alkoxy and —COOR$^{17}$, aryl wherein adjacent carbons form a ring with a methylenedioxy group, —C(O)NR$^4$R$^5$ or heteroaryl;

R$^{21}$-aryl; aryl wherein adjacent carbons form a ring with a methylenedioxy group;

R$^{41}$-heteroaryl; and heteroaryl wherein adjacent carbon atoms form a ring with a C$_3$–C$_5$ alkylene group or a methylenedioxy group;

R$^4$ and R$^5$ are independently selected from the group consisting of H, C$_1$–C$_6$ alkyl, phenyl, benzyl and C$_3$–C$_7$ cycloalkyl, or R$^4$ and R$^5$ together are —(CH$_2$)$_4$—, —(CH$_2$)$_5$— or —(CH$_2$)$_2$NR$^7$—(CH$_2$)$_2$— and form a ring with the nitrogen to which they are attached;

R$^6$ is independently selected from the group consisting of H, C$_1$–C$_6$ alkyl, phenyl, (C$_3$–C$_7$)cycloalkyl, (C$_3$–C$_7$) cycloalkyl(Cl-C$_6$)alkyl, (C$_1$–C$_6$)alkoxy(C$_1$–C$_6$)alkyl, hydroxy(C$_1$–C$_6$)alkyl and amino(C$_1$–C$_6$)alkyl;

R$^7$ is H or (C$_1$–C$_6$)alkyl;

R$^8$, R$^{10}$ and R$^{11}$ are independently selected from the group consisting of R$^1$ and —OR$^1$, provided that when the optional double bond is present, R$^{10}$ is absent;

R$^9$ is H, OH, C$_1$–C$_6$ alkoxy, halogen or halo(C$_1$–C$_6$)alkyl;

B is —(CH$_2$)$_{n3}$—, —CH$_2$—O—, —CH$_2$S—, —CH$_2$—NR$^6$—, —C(O)NR$^6$—, —NR$^6$C(O)—,

, cis or trans —(CH$_2$)$_{n4}$CR$^{12}$=CR$^{12a}$(CH$_2$)$_{n5}$ or —(CH$_2$)$_{n4}$C≡C(CH$_2$)$_{n5}$—, wherein n$_3$ is 0–5, n$_4$ and n$_5$ are independently 0–2, and R$^{12}$ and R$^{12a}$ are independently selected from the group consisting of H, C$_1$–C$_6$ alkyl and halogen;

X is —O— or —NR$^6$— when the double dotted line represents a single bond, or X is H, —OH or —NHR$^{20}$ when the bond is absent;

Y is =O, =S, (H, H), (H, OH) or (H, C$_1$–C$_6$ alkoxy) when the double dotted line represents a single bond, or when the bond is absent, Y is =O, =NOR$^{17}$, (H, H), (H, OH), (H, SH), (H, C$_1$–C$_6$ alkoxy) or (H, —NHR$^{45}$);

R$^{15}$ is absent when the double dotted line represents a single bond; R$^{15}$ is H, C$_1$–C$_6$ alkyl, —NR$^{18}$R$^{19}$ or —OR$^{17}$ when the bond is absent; or Y is

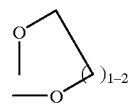

or

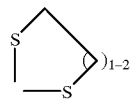

and R$^{15}$ is H or C$_1$–C$_6$ alkyl;

R$^{16}$ is C$_1$–C$_6$ lower alkyl, phenyl or benzyl;

R$^{17}$, R$^{18}$ and R$^{19}$ are independently selected from the group consisting of H, C$_1$–C$_6$ alkyl, phenyl, benzyl;

R$^{20}$ is H, C$_1$–C$_6$ alkyl, phenyl, benzyl, —C(O)R$^6$ or —SO$_2$R$^6$;

R$^{21}$ is 1 to 3 substutuents independently selected from the group consisting of hydrogen, —CF$_3$, —OCF$_3$, halogen, —NO$_2$, C$_1$–C$_6$ alkyl, C$_1$–C6alkoxy, (C$_1$–C$_6$) alkylamino, di-((C$_1$–C$_6$)alkyl)amino, amino(C$_1$–C$_6$) alkyl, (C$_1$–C$_6$)-alkylamino(C$_1$–C$_6$)alkyl, di-((C$_1$–C$_6$) alkyl)-amino(C$_1$–C$_6$)alkyl, hydroxy-(C$_1$–C$_6$)alkyl, —COOR$^{17}$, —COR$^{17}$, —NHCOR$^{16}$, —NHSO$_2$R$^{16}$, —NHSO$_2$CH$_2$CF$_3$, heteroaryl or —C(=NOR$^{17}$)R$^{18}$;

R$^{22}$ and R$^{23}$ are independently selected from the group consisting of hydrogen, R$^{24}$—(C$_1$–C$_{10}$)alkyl, R$^{24}$—(C$_2$–C$_{10}$)alkenyl, R$^{24}$—(C$_2$–C$_{10}$)alkynyl, R$^{27}$-heterocycloalkyl, R$^{25}$-aryl, R$^{25}$-aryl(C$_1$–C$_6$)alkyl, R$^{29}$—(C$_3$–C$_7$)cycloalkyl, R$^{29}$—(C$_3$–C$_7$)cycloalkenyl, —OH, —OC(O)R$^{30}$, —C(O)OR$^{30}$, —C(O)R$^{30}$, —C(O)NR$^{30}$R$^{31}$, —NR$^{30}$R$^{31}$, —NR$^{30}$C(O)R$^{31}$, —NR$^{30}$C(O)NR$^{31}$R$^{32}$, —NHSO$_2$R$^{30}$, —OC(O)NR$^{30}$R$^{31}$, R$^{24}$—(C$_1$–C$_{10}$)alkoxy, R$^{24}$—(C$_2$–C$_{10}$)-alkenyloxy, R$^{24}$—(C$_2$–C$_{10}$)alkynyloxy, R$^{27}$-heterocycloalkyloxy, R$^{29}$—(C$_3$–C$_7$)cycloalkyloxy, R$^{29}$—(C$_3$–C$_7$)cycloalkenyloxy, R$^{29}$—(C$_3$–C$_7$)cycloalkyl-NH—, —NHSO$_2$NHR$^{16}$ and —CH(=NOR$^{17}$);

or R$^{22}$ and R$^{10}$ together with the carbon to which they are attached, or R$^{23}$ and R$^{11}$ together with the carbon to which they are attached, independently form a R$^{42}$-substituted carbocyclic ring of 3–10 atoms, or a R$^{42}$-substituted heterocyclic ring of 4–10 atoms wherein 1–3 ring members are independently selected from the group consisting of —O—, —NH— and —SO$_{0-2}$—, provided that when R$^{22}$ and R$^{10}$ form a ring, the optional double bond is absent;

R$^{24}$ is 1, 2 or 3 substituents independently selected from the group consisting of hydrogen, halogen, —OH, (C$_1$–C$_6$)alkoxy, R$^{35}$-aryl, (C$_1$–C$_{10}$)-alkyl-C(O)—, (C$_2$–C$_{10}$)-alkenyl-C(O)—, (C$_2$–C$_{10}$)alkynyl-C(O)—, heterocycloalkyl, R$^{26}$—(C$_3$–C$_7$)cycloalkyl, R$^{26}$—(C$_3$–C$_7$)cycloalkenyl, —OC(O)R$^{30}$, —C(O)OR$^{30}$, —C(O)R$^{30}$, —C(O)NR$^{30}$R$^{31}$, —NR$^{30}$R$^{31}$, —NR$^{30}$C(O)R$^{31}$, —NR$^{30}$C(O)NR$^{31}$R$^{32}$, —NHSO$_2$R$^{30}$, —OC(O)NR$^{30}$R$^{31}$, R$^{24}$—(C$_2$–C$_{10}$)-alkenyloxy, R$^{24}$—(C$_2$–C$_{10}$)alkynyloxy, R$^{27}$-heterocycloalkyloxy, R$^{29}$—(C$_3$–C$_7$)-cycloalkyloxy, R$^{29}$—(C$_3$–C$_7$)cycloalkenyloxy, R$^{29}$—(C$_3$–C$_7$)cycloalkyl-NH—, —NHSO$_2$NHR$^{16}$ and —CH(=NOR$^{17}$);

R$^{25}$ is 1, 2 or 3 substituents independently selected from the group consisting of hydrogen, heterocycloalkyl, halogen, —COOR$^{36}$, —CN, —C(O)NR$^{37}$R$^{38}$, —NR$^{39}$C(O)R$^{40}$, —OR$^{36}$, (C$_3$–C$_7$)cycloalkyl, (C$_3$–C$_7$) cycloalkyl-C$_1$–C$_6$)alkyl, (C$_1$–C$_6$)alkyl(C$_3$–C$_7$)

cycloalkyl-($C_1$–$C_6$)alkyl, halo($C_1$–$C_6$)alkyl($C_3$–$C_7$) cycloalkyl($C_1$–$C_6$)alkyl, hydroxy($C_1$–$C_6$)alkyl, ($C_1$–$C_6$)alkoxy($C_1$–$C_6$)alkyl, and $R^{41}$-heteroaryl; or two $R^{25}$ groups on adjacent ring carbons form a fused methylenedioxy group $R^{26}$ is 1, 2, or 3 substituents independently selected from the group consisting of hydrogen, halogen and ($C_1$–$C_6$) alkoxy;

$R^{27}$ is 1, 2 or 3 substituents independently selected from the group consisting of hydrogen, $R^{28}$—($C_1$–$C_{10}$)alkyl, $R^{28}$—($C_2$–$C_{10}$)alkenyl, $R^{28}$—($C_2$–$C_{10}$)alkynyl, $R^{28}$ is hydrogen, —OH or ($C_1$–$C_6$)alkoxy;

$R^{29}$ is 1, 2 or 3 substituents independently selected from the group consisting of hydrogen, ($C_1$–$C_6$)alkyl, —OH, ($C_1$–$C_6$)alkoxy and halogen;

$R^{30}$, $R^{31}$ and $R^{32}$ are independently selected from the group consisting of hydrogen, ($C_1$–$C_{10}$)-alkyl, ($C_1$–$C_6$) alkoxy($C_1$–$C_{10}$)-alkyl, $R^{25}$-aryl($C_1$–$C_6$)-alkyl, $R^{33}$—($C_3$–$C_7$)cycloalkyl, $R^{34}$—($C_3$–$C_7$)cycloalkyl($C_1$–$C_6$) alkyl, $R^{25}$-aryl, heterocycloalkyl, heteroaryl, heterocycloalkyl($C_1$–$C_6$)alkyl and heteroaryl($C_1$–$C_6$) alkyl;

$R^{33}$ is hydrogen, ($C_1$–$C_6$)alkyl, OH—($C_1$–$C_6$)alkyl or ($C_1$–$C_6$)alkoxy;

$R^{35}$ is 1 to 4 substituents independently selected from the group consisting of hydrogen, ($C_1$–$C_6$)alkyl, —OH, halogen, —CN, ($C_1$–$C_6$)alkoxy, trihalo($C_1$–$C_6$)alkoxy, ($C_1$–$C_6$)alkylamino, di(($C_1$–$C_6$)alkyl)amino, —OCF$_3$, OH—($C_1$–$C_6$)alkyl, —CHO, —C(O)($C_1$–$C_6$)-alkylamino, —C(O)di(($C_1$–$C_6$)alkyl)amino, —NH$_2$, —NHC(O)($C_1$–$C_6$)alkyl and —N(($C_1$–$C_6$)alkyl)C(O) ($C_1$–$C_6$)alkyl;

$R^{36}$ is hydrogen, ($C_1$–$C_6$)alkyl, halo($C_1$–$C_6$)alkyl, dihalo ($C_1$–$C_6$)alkyl or trifluoro($C_1$–$C_6$)alkyl, $R^{37}$ and $R^{38}$ are independently selected from the group consisting of hydrogen, ($C_1$–$C_6$)alkyl, aryl($C_1$–$C_6$) alkyl, phenyl and ($C_3$–$C_{15}$)cycloalkyl, or $R^{37}$ and $R^{38}$ together are —(CH$_2$)$_4$—, —(CH$_2$)$_5$— or —(CH$_2$)$_2$—NR$^{39}$—(CH$_2$)$_2$— and form a ring with the nitrogen to which they are attached;

$R^{39}$ and $R^{40}$ are independently selected from the group consisting of hydrogen, ($C_1$–$C_6$)alkyl, aryl($C_1$–$C_6$) alkyl, phenyl and ($C_3$–$C_{15}$)-cycloalkyl, or $R^{39}$ and $R^{40}$ in the group —NR$^{39}$C(O)R$^{40}$, together with the carbon and nitrogen atoms to which they are attached, form a cyclic lactam having 5–8 ring members;

$R^{41}$ is 1 to 4 substituents independently selected from the group consisting of hydrogen, ($C_1$–$C_6$)alkyl, ($C_1$–$C_6$) alkoxy, ($C_1$–$C_6$)alkylamino, di(($C_1$–$C_6$)alkyl)amino, —OCF$_3$, OH—($C_1$–$C_6$)alkyl, —CHO and phenyl;

$R^{42}$ is 1 to 3 substituents independently selected from the group consisting of hydrogen, —OH, ($C_1$–$C_6$)alkyl and ($C_1$–$C_6$)alkoxy;

$R^{43}$ is —NR$^{30}$R$^{31}$, —NR$^{30}$C(O)R$^{31}$, —NR$^{30}$ C(O) NR$^{31}$R$^{32}$, —NHSO$_2$R$^{30}$ or —NHCOOR$^{17}$;

$R^{44}$ is H, $C_1$–$C_6$ alkoxy, —SOR$^{16}$, —SO$_2$R$^{17}$, —C(O) OR$^{17}$, —C(O)NR$^{18}$R$^{19}$, $C_1$–$C_6$ alkyl, halogen, fluoro ($C_1$–$C_6$)alkyl, difluoro($C_1$–$C_6$)alkyl, trifluoro($C_1$–$C_6$) alkyl, $C_3$–$C_7$ cycloalkyl, $C_2$–$C_6$ alkenyl, aryl($C_1$–$C_6$) alkyl, aryl($C_2$–$C_6$)alkenyl, heteroaryl($C_1$–$C_6$)alkyl, heteroaryl($C_2$–$C_6$)alkenyl, hydroxy($C_1$–$C_6$)alkyl, amino($C_1$–$C_6$)alkyl, aryl, thio($C_1$–$C_6$)alkyl, ($C_1$–$C_6$) alkoxy($C_1$–$C_6$)alkyl or ($C_1$–$C_6$)alkylamino($C_1$–$C_6$) alkyl; and $R^{45}$ is H, $C_1$–$C_6$ alkyl, —COOR$^{16}$ or —SO$_2$.

$R^2$, $R^8$, $R^{10}$ and $R^{11}$ are each preferably hydrogen. $R^3$ preferably is hydrogen, OH, $C_1$–$C_6$ alkoxy, —NHR$^{18}$ or $C_1$–$C_6$ alkyl. The variable n is preferably zero. $R^9$ is preferably H, OH or alkoxy. $R^1$ is preferably $C_1$–$C_6$ alkyl, more preferably methyl. The double dotted line preferably represents a single bond; X is preferably —O— and Y is preferably =O or (H, —OH). B is preferably trans —CH=CH—. Het is preferably pyridyl, substituted pyridyl, quinolyl or substituted quinolyl. Preferred substituents (W) on Het are $R^{21}$-aryl, $R^{41}$-heteroaryl or alkyl. More preferred are compounds wherein Het is 2-pyridyl substituted in the 5-position by $R^{21}$-aryl, $R^{41}$-heteroaryl or alkyl, or 2-pyridyl substituted in the 6-position by alkyl. $R^{34}$ is preferably (H,H) or (H,OH).

$R^{22}$ and $R^{23}$ are preferably selected from OH, ($C_1$–$C_{10}$) alkyl, ($C_2$–$C_{10}$)-alkenyl, ($C_2$–$C_{10}$)-alkynyl, trifluoro ($C_1$–$C_{10}$)alkyl, trifluoro($C_2$–$C_{10}$)-alkenyl, trifluoro ($C_2$–$C_{10}$)alkynyl, ($C_3$–$C_7$)-cycloalkyl, $R^{25}$-aryl, $R^{25}$-aryl($C_1$–$C_6$)alkyl, $R^{25}$-arylhydroxy($C_1$–$C_6$)alkyl, $R^{25}$-aryl-alkoxy-($C_1$–$C_6$)alkyl, ($C_3$–$C_7$)cycloalkyl-($C_1$–$C_6$) alkyl, ($C_1$–$C_{10}$)alkoxy, ($C_3$–$C_7$)cycloalkyloxy, ($C_1$–$C_6$) alkoxy($C_1$–$C_6$)alkyl, OH—($C_1$–$C_6$)alkyl, trifluoro ($C_1$–$C_{10}$)alkoxy and $R^{27}$-heterocycloalkyl($C_1$–$C_6$) alkyl. More preferred are compounds wherein $R^{22}$ and $R^{23}$ are independently selected from the group consisting of ($C_1$–$C_{10}$)alkyl and OH—($C_1$–$C_6$)alkyl.

Thrombin receptor antagonist compounds of the present invention have anti-thrombotic, anti-platelet aggregation, antiatherosclerotic, antirestenotic and anti-coagulant activity. Thrombosis-related diseases treated by the compounds of this invention are thrombosis, atherosclerosis, restenosis, hypertension, angina pectoris, arrhythmia, heart failure, myocardial infarction, glomerulonephritis, thrombotic and thromboembolytic stroke, peripheral vascular diseases, other cardiovascular diseases, cerebral ischemia, inflammatory disorders and cancer, as well as other disorders in which thrombin and its receptor play a pathological role.

The compounds of the invention which bind to cannabinoid (CB2) receptors are useful in the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

This invention also relates to a method of using a compound of formula I in the treatment of thrombosis, platelet aggregation, coagulation, cancer, inflammatory diseases or respiratory diseases, comprising administering a compound of formula I to a mammal in need of such treatment. In particular, the present invention relates to a method of using a compound of formula I in the treatment of thrombosis, atherosclerosis, restenosis, hypertension, angina pectoris, arrhythmia, heart failure, myocardial infarction, glomerulonephritis, thrombotic stroke, thromboembolytic stroke, peripheral vascular diseases, cerebral ischemia, cancer, rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, reversible airway obstruction, chronic asthma or bronchitis. It is contemplated that a compound of this invention may be useful in treating more than one of the diseases listed.

In another aspect, the invention relates to a pharmaceutical composition comprising a therapeutically effective amount of a compound of formula I in a pharmaceutically acceptable carrier.

DETAILED DESCRIPTION

Unless otherwise defined, the term "alkyl" or "lower alkyl" means straight or branched alkyl chains of 1 to 6 carbon atoms and "alkoxy" similarly refers to alkoxy groups having 1 to 6 carbon atoms.

Fluoroalkyl, difluoroalkyl and trifluoroalkyl mean alkyl chains wherein the terminal carbon is substituted by 1, 2 or 3 fluoroatoms, e.g., —$CF_3$, —$CH_2CF_3$, —$CH_2CHF_2$ or —$CH_2CH_2F$. Haloalkyl means an alkyl chain substituted by 1 to 3 halo atoms.

"Alkenyl" means straight or branched carbon chains of carbon atoms having one or more double bonds in the chain, conjugated or unconjugated. Similarly, "alkynyl" means straight or branched carbon chains of carbon atoms having one or more triple bonds in the chain. Where an alkyl, alkenyl or alkynyl chain joins two other variables and is therefore bivalent, the terms alkylene, alkenylene and alkynylene are used. Unless otherwise defined, alkenyl and alkynyl chains comprise 1 to 6 carbon atoms.

Substitution on alkyl, alkenyl and alkynyl chains depends on the length of the chain, and the size and nature of the substituent. Those skilled in the art will appreciate that while longer chains can accommodate multiple substituents, shorter alkyl chains, e.g., methyl or ethyl, can have multiple substitution by halogen, but otherwise are likely to have only one or two substituents other than hydrogen. Shorter unsaturated chains, e.g., ethenyl or ethynyl, are generally unsubstituted or substitution is limited to one or two groups, depending on the number of available carbon bonds.

"Cycloalkyl" means a saturated carbon ring of 3 to 7 carbon atoms, while "cycloalkylene" refers to a corresponding bivalent ring, wherein the points of attachment to other groups include all positional and stereoisomers. "Cycloalkenyl" refers to a carbon ring of 3 to 7 atoms and having one or more unsaturated bonds, but not having an aromatic nature.

"Heterocycloalkyl" means saturated rings of 5 or 6 atoms comprised of 4 to 5 carbon atoms and 1 or 2 heteroatoms selected from the group consisting of —O—, —S— and —$NR^7$— joined to the rest of the molecule through a carbon atom. Examples of heterocycloalkyl groups are 2-pyrrolidinyl, tetrahydrothiophen-2-yl, tetrahydro-2-furanyl, 4-piperidinyl, 2-piperazinyl, tetrahydro-4-pyranyl, 2-morpholinyl and 2-thiomorpholinyl.

"Halogen" refers to fluorine, chlorine, bromine or iodine radicals.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

"Dihydroxy($C_1$–$C_6$)alkyl" refers to an alkyl chain substituted by two hydroxy groups on two different carbon atoms.

"Aryl" means phenyl, naphthyl, indenyl, tetrahydronaphthyl or indanyl.

"Heteroaryl" means a single ring or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included, as well as compounds wherein a ring nitrogen is substituted by a $C_1$–$C_4$ alkyl group to form a quaternary amine. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. W-substituted heteroaryl refers to such groups wherein substitutable ring carbon atoms have a substituent as defined above, or where adjacent carbon atoms form a ring with an alkylene group or a methylenedioxy group, or where a nitrogen in the Het ring can be substituted with $R^{21}$-aryl or an optionally substituted alkyl substituent as defined in W.

The term "Het" is exemplified by the single ring and benzofused heteroaryl groups as defined immediately above, as well as tricyclic groups such as benzoquinolinyl (e.g., 1,4 or 7,8) or phenanthrolinyl (e.g., 1,7; 1,10; or 4,7). Het groups are joined to group B by a carbon ring member, e.g., Het is 2-pyridyl, 3-pyridyl or 2-quinolyl.

Examples of heteroaryl groups wherein adjacent carbon atoms form a ring with an alkylene group are 2,3-cyclopentenopyridine, 2,3-cyclohexenopyridine and 2,3-cycloheptenopyridine.

The term "optional double bond" refers to the bond shown by the single dotted line in the middle ring of the structure shown for formula I. The term "optional single bond" refers to the bond shown by the double dotted line between X and the carbon to which Y and $R^{15}$ are attached in the structure of formula I.

The above statements, wherein, for example, $R^4$ and $R^5$ are said to be independently selected from a group of substituents, means that $R^4$ and $R^5$ are independently selected, but also that where an $R^4$ or $R^5$ variable occurs more than once in a molecule, those occurrences are independently selected. Those skilled in the art will recognize that the size and nature of the substituent(s) will affect the number of substituents which can be present.

Compounds of the invention have at least one asymmetrical carbon atom and therefore all isomers, including diastereomers and rotational isomers are contemplated as being part of this invention. The invention includes (+)- and (−)-isomers in both pure form and in admixture, including racemic mixtures. Isomers can be prepared using conventional techniques, either by reacting optically pure or optically enriched starting materials or by separating isomers of a compound of formula I.

Typical preferred compounds of the present invention have the following stereochemistry:

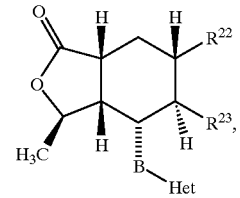

with compounds having that absolute stereochemistry being more preferred.

Those skilled in the art will appreciate that for some compounds of formula I, one isomer will show greater pharmacological activity than other isomers.

Compounds of the invention with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, lithium, gold and silver salts. Also included are salts formed with pharmaceutically acceptable amines such as ammonia, alkyl amines, hydroxyalkylamines, N-methylglucamine and the like.

Compounds of the present invention are generally prepared by processes known in the art, for example by the processes described below.

Compounds of formula IA, wherein n is 0, the optional double bond is not present, the single bond is present between X and the carbon to which Y is attached, X is —O—, Y is =O, B is —CH=CH—, Het is W-substituted pyridyl, $R^3$, $R^8$, $R^9$, $R^{10}$ and $R^{11}$ are each hydrogen, and $R^1$ and $R^2$ are as defined above can be prepared by condensing an aldehyde of formula II, wherein the variables are as defined above, with a phosphonate of formula III, wherein W is as defined above:

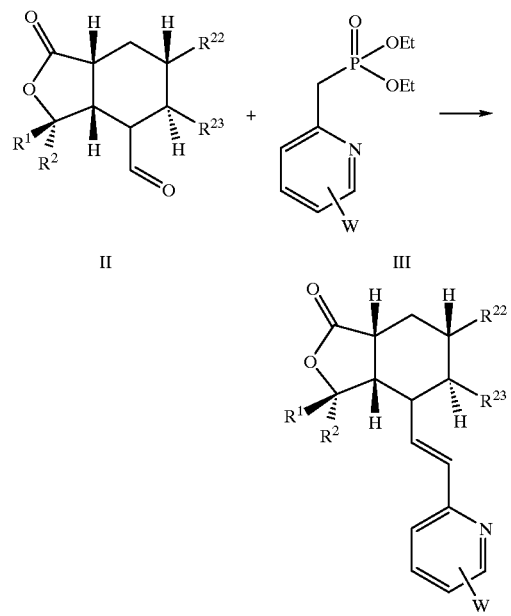

Similar processes may be used to prepare compounds comprising other optionally substituted Het groups. Those skilled in the art will also recognize that the processes are equally applicable to preparing optically active or racemic compounds.

Compounds of formula IA can be converted to the corresponding compounds wherein $R^3$ is OH by treatment with Davis reagent ((1S)-(+)-(10-camphorsulfonyl)-oxaziridine) and LHMDS (Lithium bis(trimethylsilyl)amide).

Aldehydes of formula II can be prepared from dienoic acids, for example compounds of formula IIa, wherein $R^1$ is H and $R^2$ is methyl can be prepared according to the following reaction scheme.

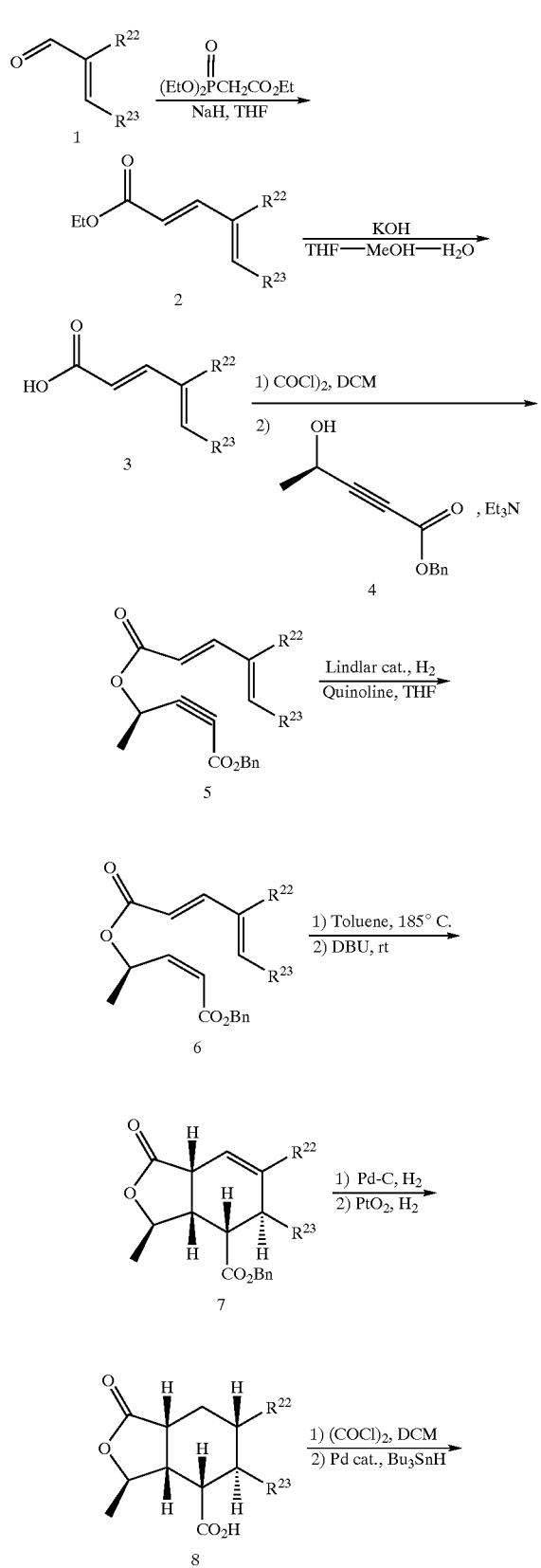

Scheme 1

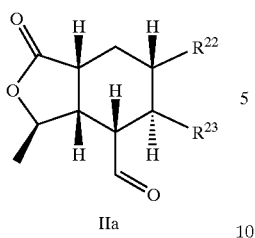

IIa

The alkyne of formula 4, prepared by known methods, is esterified with the dienoic acid of formula 3 using standard conditions to yield the ester 5. Selective reduction of the triple bond of 5 using Lindlar catalyst under hydrogen gives the intermediate 6, which upon thermal cyclization at about 185° C., followed by base treatment, gives the intermediate 7. The ester 7 is subjected to hydrogenation in the presence of platinum oxide to generate the intermediate saturated carboxylic acid, treatment of which with oxalyl chloride gives the corresponding acid chloride which is converted to the aldehyde IIa by reduction using tributyltin hydride in the presence of Palladium catalyst.

Dienoic acids of formula 3 are commercially available or are readily prepared.

Aldehydes of formula II also can be prepared by a thiopyran ring opening, for example compounds of formula IIa as defined above can be prepared according to the following reaction scheme.

Scheme 2

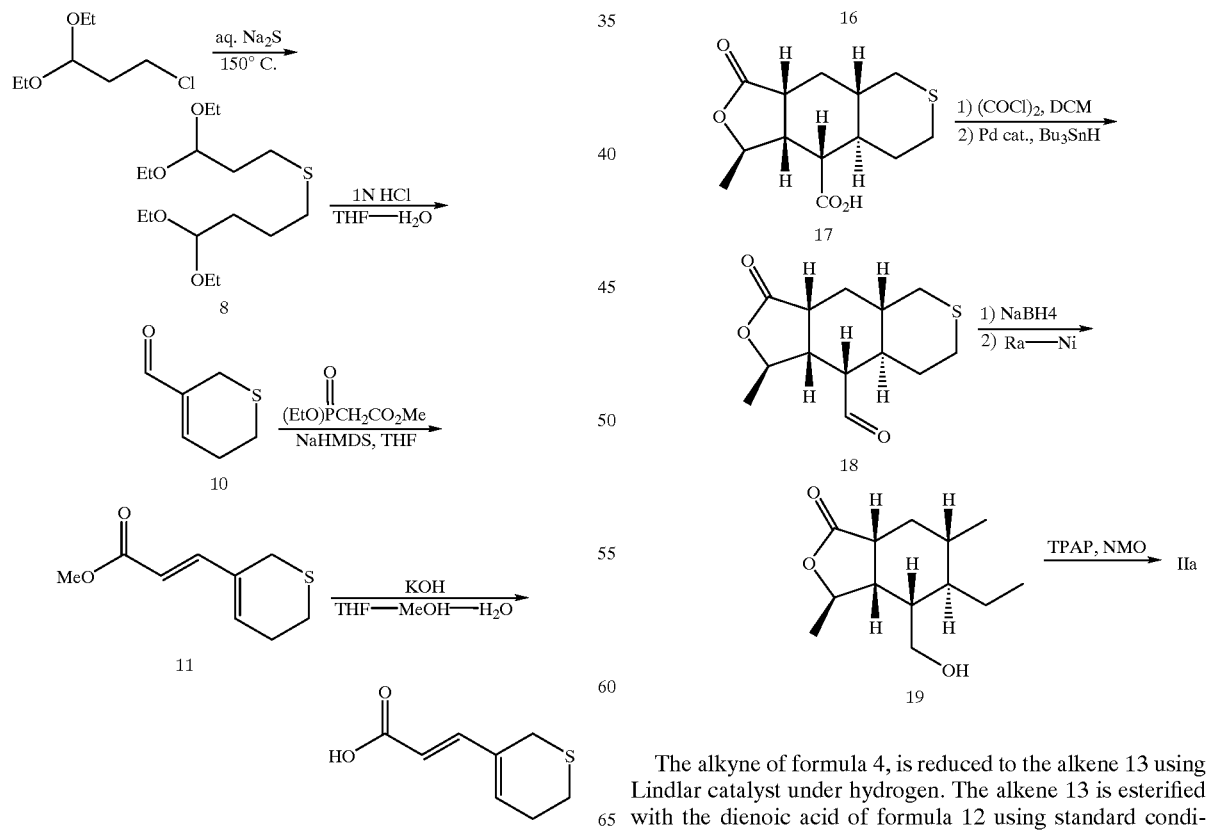

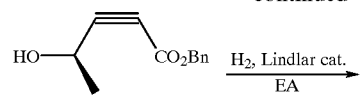

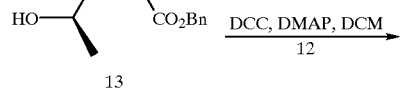

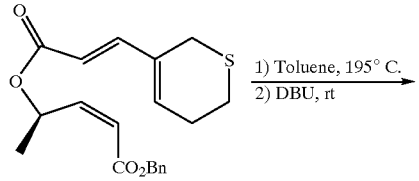

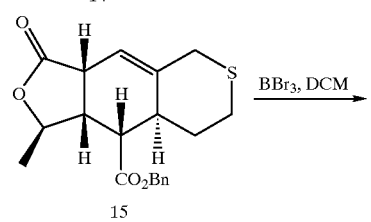

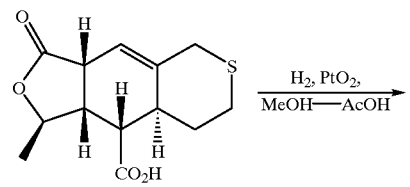

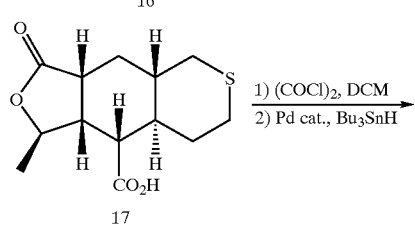

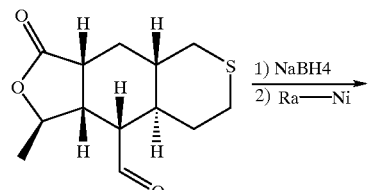

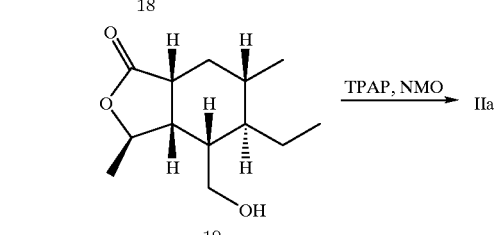

The alkyne of formula 4, is reduced to the alkene 13 using Lindlar catalyst under hydrogen. The alkene 13 is esterified with the dienoic acid of formula 12 using standard conditions to yield the ester 14. Thermal cyclization at about 185° C., followed by base treatment, gives the intermediate 15.

The ester 15 is converted to the intermediate carboxylic acid, and the double bond is reduced by hydrogenation in the presence of a platinum catalyst. The acid is then treated with oxalyl chloride to obtain the corresponding acid chloride, which is converted to the aldehyde 18 by reduction using tributyltin hydride in the presence of Palladium catalyst. The aldehyde moiety on 18 is treated with a reducing agent such as $NaBH_4$, and the sulfur-containing ring is then opened by treatment with a reagent such as Raney nickel to obtain the alcohol 19. The alcohol is then oxidized to the aldehyde, IIa, using tetrapropylammonium perruthenate (TPAP) in the presence of 4-methylmorpholine N-oxide (NMO).

Phosphonates of formula III wherein W is aryl or $R^{21}$-aryl can be prepared by a process similar to that described immediately below for preparing the trifluoromethy-phenyl-substituted compound, IIIa.

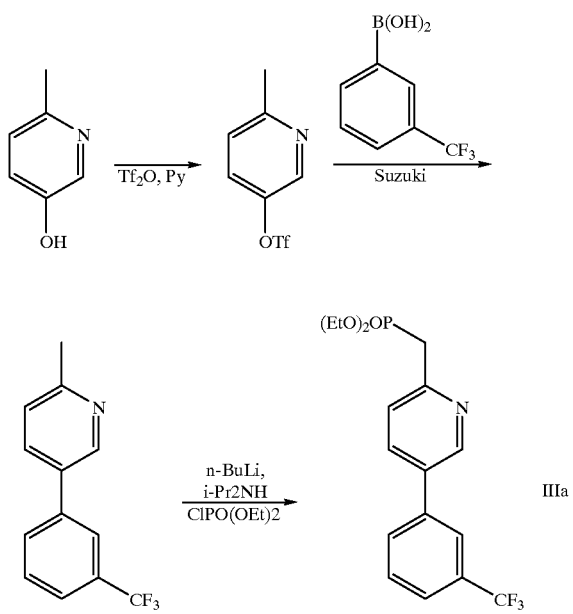

Commercially available hydroxypyridine derivative is converted to the corresponding triflate using triflic anhydride, which is then coupled with commercially available boronic acid in the presence of Pd(0) under Suzuki conditions. The resulting product is converted to the phosphonate by treatment with n-butyllithium followed by quenching with diethylchlorophosphonate.

Alternatively, compounds of formula I wherein W is optionally substituted aryl can be prepared from compounds of formula I wherein W is —OH using a triflate intermediate. For example, 3-hydroxy-6-methylpyridine is treated with triisopropylsilyl chloride, and the resultant hydroxy-protected compound is converted to the phosphonate as described above for preparing intermediate IIIa. The triisopropylsilyl-protected intermediate is then reacted with intermediate II and the protecting group is removed under standard conditions. The resultant compound of formula I wherein W is OH is then treated with triflic anhydride at room temperature in a solvent such as $CH_2Cl_2$; the triflate is then reacted with an optionally substituted arylboronic acid, e.g., optionally substituted phenylboronic acid, in a solvent such as toluene, in the presence of $Pd(PPh_3)_4$ and a base such a $K_2CO_3$ at elevated temperatures and under an inert atmosphere.

Compounds of formula I wherein W is a substituted hydroxy group (e.g., benzyloxy) can be prepared from compounds of formula I wherein W is hydroxy by refluxing in a suitable solvent such as acetone with a halogen-substituted compound such as optionally substituted benzyl bromide in the presence of a base such as $K_2CO_3$.

Compounds of formula I wherein Het is substituted by W through a carbon atom (e.g., wherein W is alkyl, alkenyl or arylalkyl) or a nitrogen atom (i.e., —$NR^4R^5$) can be prepared as shown in Scheme 3 using a compound of formula I wherein W is chloroalkyl as an intermediate. Compounds of formula I wherein W is a polar group such as hydroxy alkyl, dihydroxyalkyl, —COOH, dimethylamino and —COH can be prepared as shown in Scheme 4, wherein the starting material is a compound of formula I wherein W is alkenyl. The following Schemes 3 and 4 show well-known reaction conditions for preparing various W-substituted compounds wherein X is —O—, Y is =O, $R^{15}$ is absent, $R^1$ is methyl, $R^2$, $R^3$, $R^9$, $R^{10}$ and $R^{11}$ are each H, B is —CH=CH—, and Het is 2-pyridyl.

Scheme 3

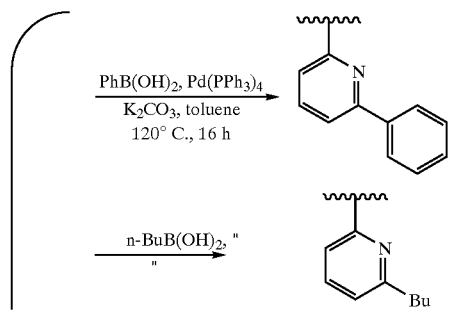

-continued
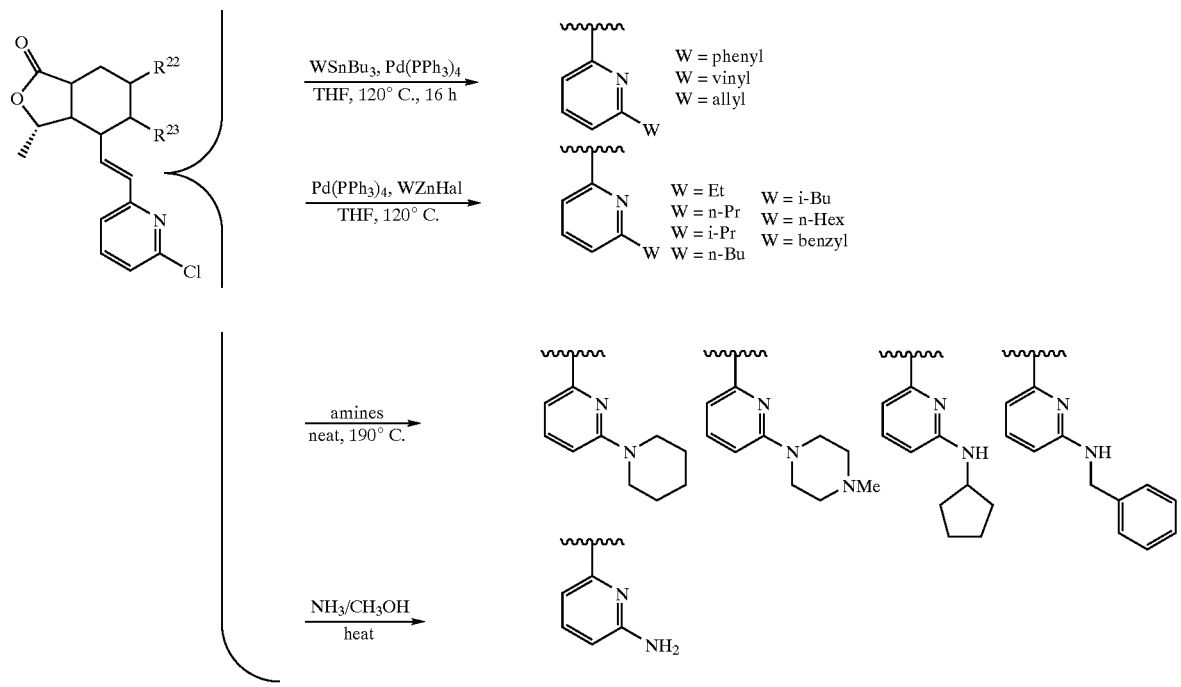
Scheme 4
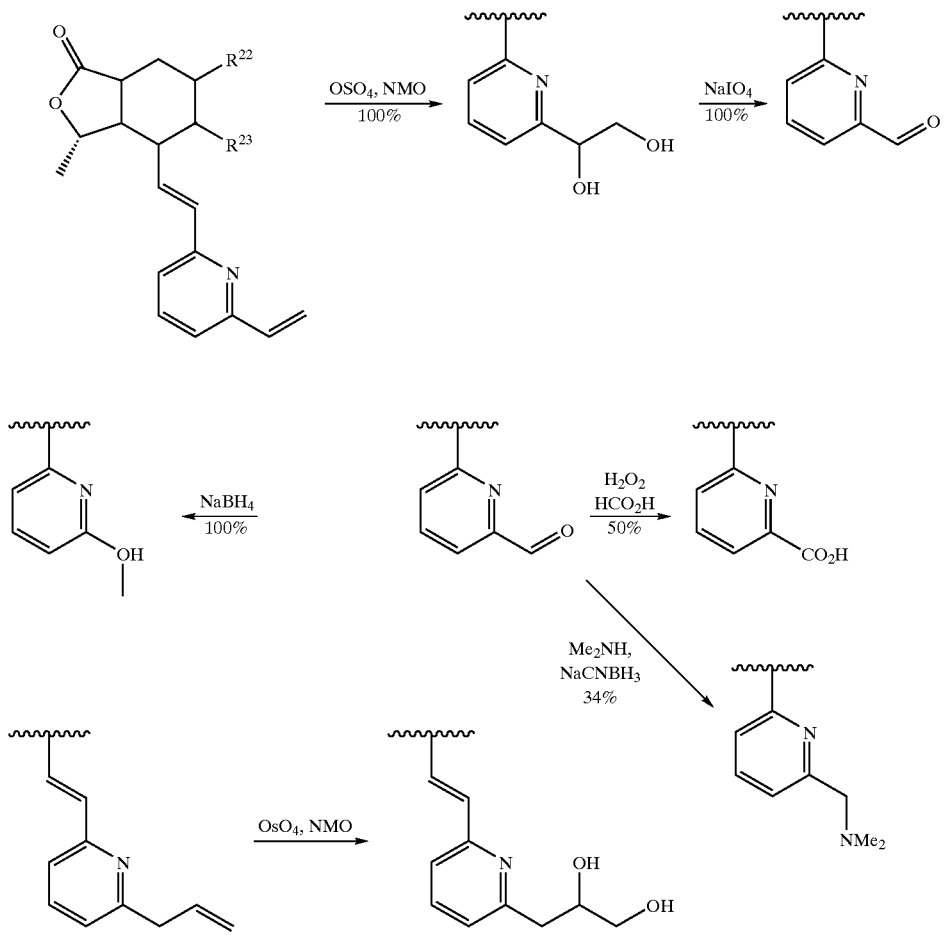

Those skilled in the art will appreciate that similar reactions to those described in the above schemes may be carried out on other compounds of formula I as long as substituents present would not be susceptible to the reaction conditions described.

Compounds of formula I wherein the optional single bond (represented by the double dotted line) is absent, X is OH, Y is OH, $R^{15}$ is H and the remaining variables are as defined above can be prepared by treating corresponding compounds wherein the optional single bond is present, X is —O—, Y is =O and $R^{15}$ is absent, with a reducing agent such as LAH.

Compounds of formula I wherein the optional single bond is present, X is —O—, Y is (H, OH), $R^{15}$ is absent and the remaining variables are as defined above can be prepared by treating corresponding compounds wherein the optional single bond is present, X is —O—, Y is =O and $R^{15}$ is absent, with a reagent such as DIBAL. The resultant compounds wherein Y is (H, OH) can be converted to the corresponding compounds wherein Y is (H, alkoxy) by reacting the hydroxy compound with an appropriate alkanol in the presence of a reagent such as $BF_3.OEt_2$. A compound wherein Y is (H, OH) can also be converted to the corresonding compound wherein Y is (H, H) by treating the hydroxy compound with $BF_3.OEt_2$ and $Et_3SiH$ in an inert solvent such as $CH_2Cl_2$ at low temperatures.

Compounds of formula I wherein $R^9$ is hydrogen can be converted to the corresponding compound wherein $R^9$ is hydroxy by heating with an oxidizing agent such as $SeO_2$.

Compounds of formula IB, wherein $R^2$ is H, $R^3$ is H or OH, and $W^1$ is $R^{21}$-aryl, $R^{41}$-heteroaryl, amino or hydroxy-lamino derivatives, are prepared from compounds of formula 1A wherein W is 5-bromo (compounds of formula 23 or 24) using a variety of standard chemical transformations, e.g. the Suzuki reaction, Stille coupling, and Buchwald amination. Reaction Scheme 5 shows the process from the 2,5-dibromopyridine:

Scheme 5

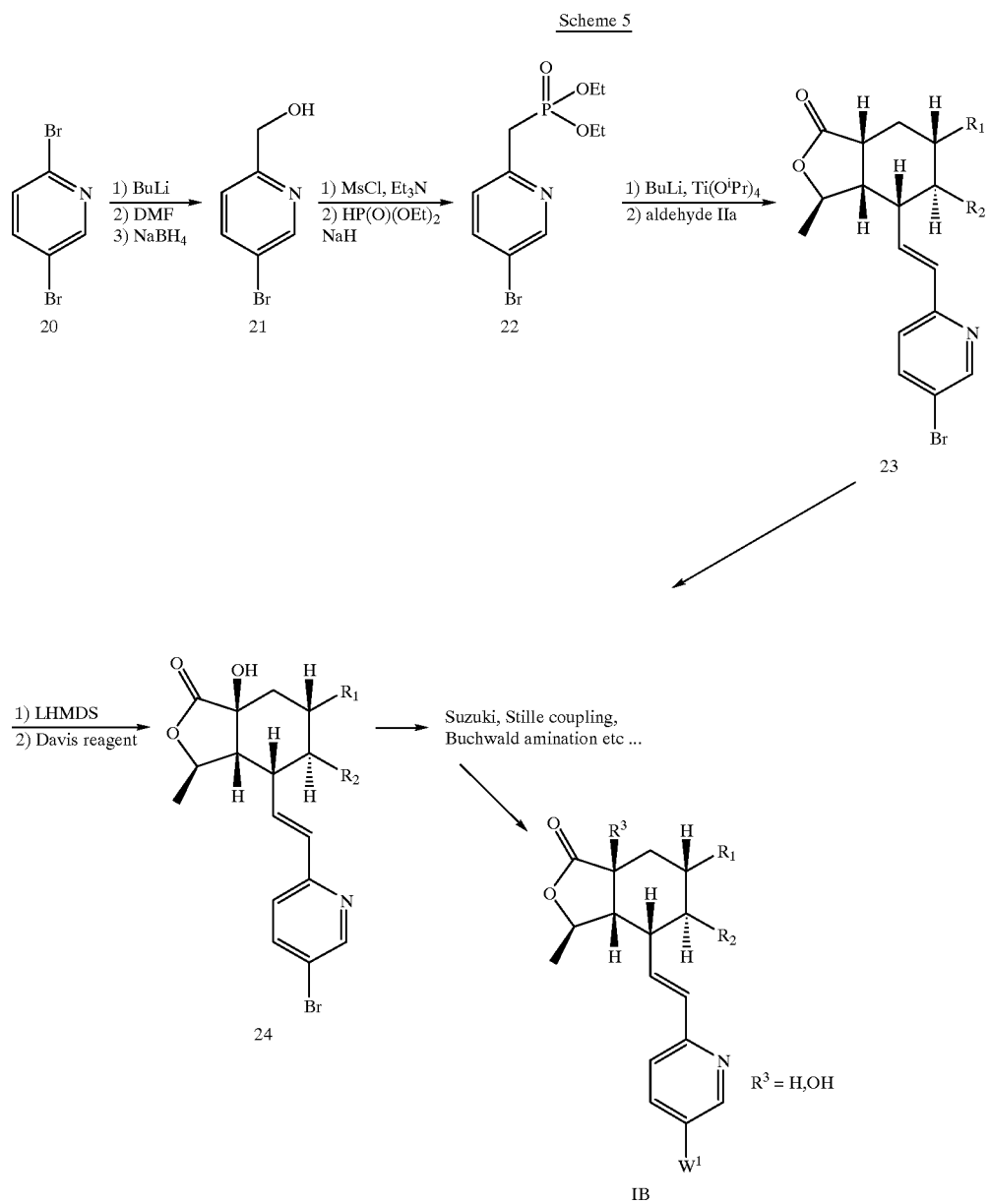

The phosphonate 22 is prepared from the known alcohol 21 by a two step transformation: the alcohol is treated with $CH_3SO_2Cl$ to provide the mesylate, which is then displaced with sodium diethylphosphite to provide 22. Intermediate 23 can also be α-hydroxylated using Davis reagent to provide alcohol 24. Both 23 and 24 can be converted into diverse analogs as shown in Scheme 6:

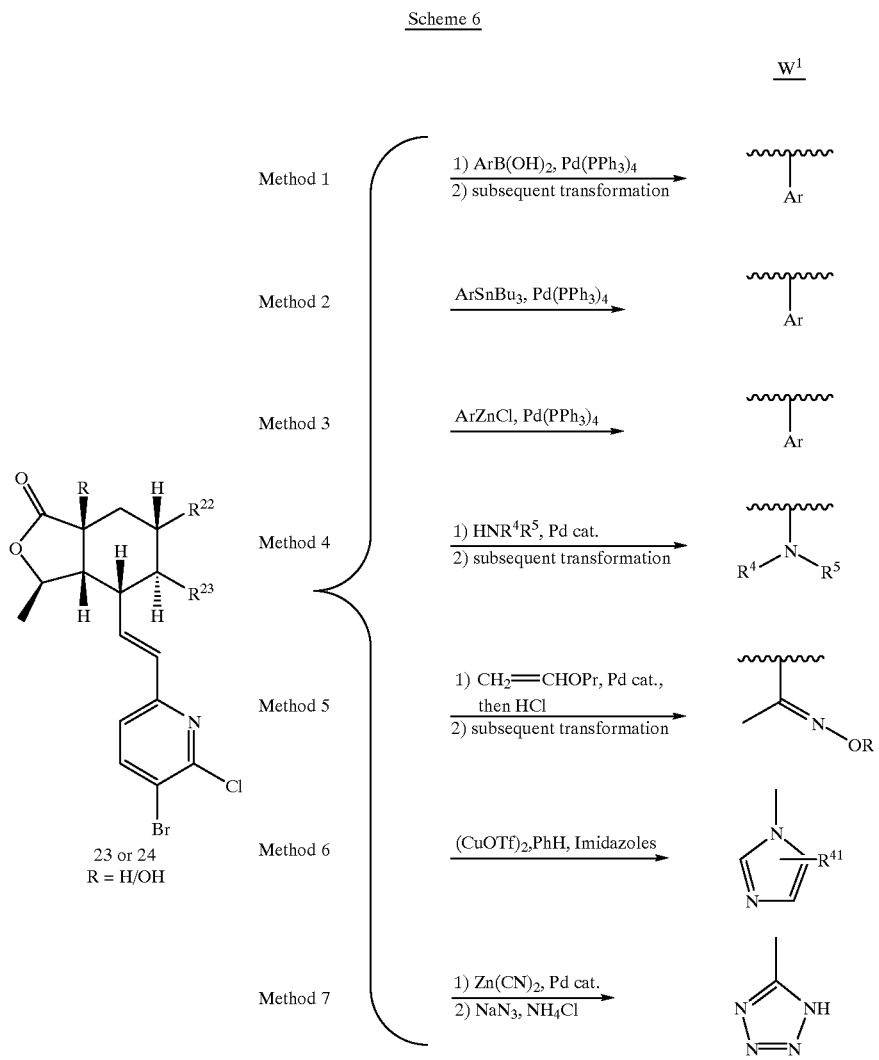

A shown in Scheme 6, the bromide (23 or 24) can be coupled with boronic acids under palladium catalysis condition (method 1). If the boronic acid possesses a functional group, it can be subsequently transformed. Similarly, aryltin compounds (method 2), aryl-zinc compounds (method 3) and amines (method 4) can be coupled. Heck reaction with vinyl ethers can introduce a keto-group, which can be subsequently functionalized (method 5). Imidazoles can be coupled using Copper(I) triflate as catalyst (method 6). The bromide can also be converted to a cyanide which can be subsequently transformed, for example to a tetrazole (method 7).

Using a Diels-Alder strategy as shown in Scheme 7, a variety of dienoic acids 3 can be coupled with alcohol 25 and the ester 26 can be subjected to thermal cyclization to provide the Diels-Alder product IC:

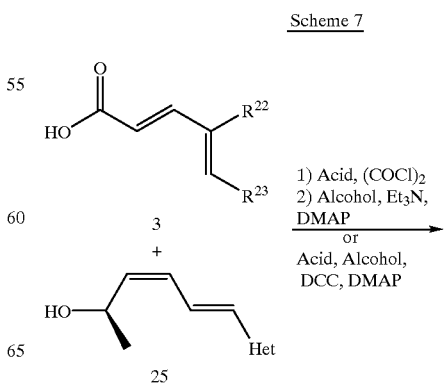

-continued

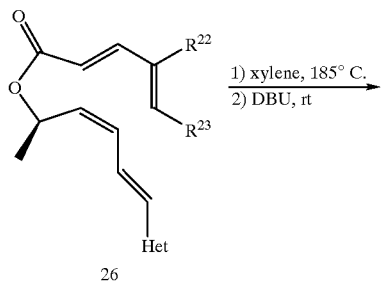

26

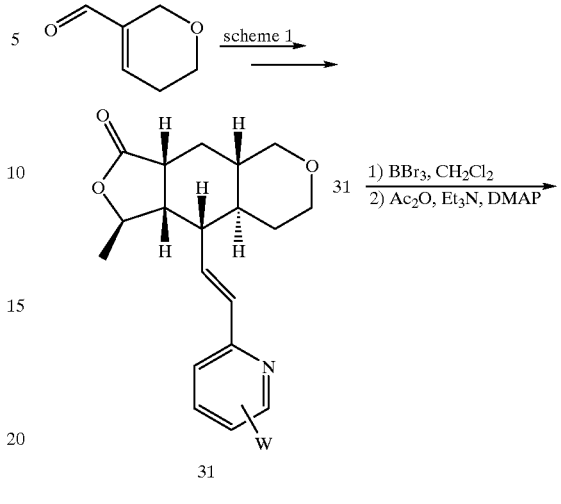

Alcohol 25 is prepared as follows:

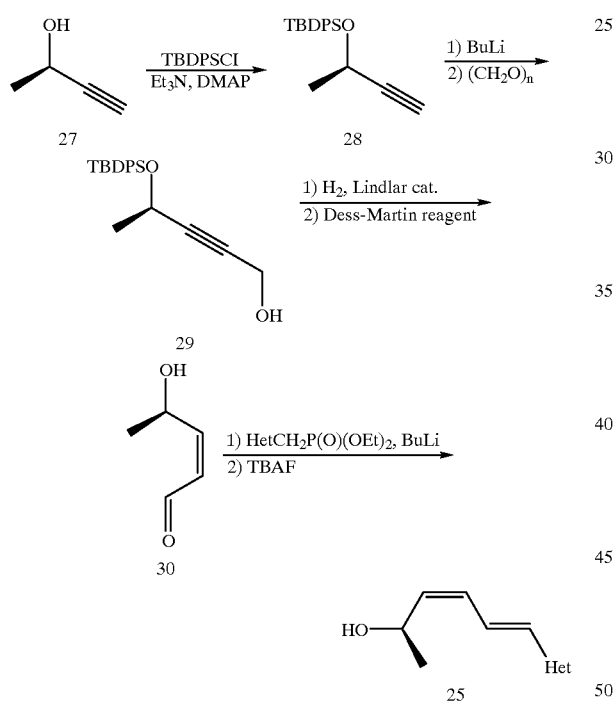

Alcohol 25 is prepared from the readily available (R)-(+)-3-butyn-2-ol 27. The alcohol is protected as its TBDPS ether, the alkyne is deprotonated and quenched with paraformaldehyde to provide alcohol 29. The alkyne is reduced to cis-alkene using Lindlar catalyst in presence of quinoline and the allylic alcohol was oxidized to provide the aldehyde 30, which is converted to the alcohol 25.

Compounds of formula ID wherein $R^{22}$ is —CH$_2$OC(O)CH$_3$ or a derivative thereof, $R^{23}$ is ethyl, $R^2$ is H and the remaining variables are as defined for IA can be prepared from the corresponding tetrahydropyran analog by opening the ring. The compounds of formula ID can be converted to other compounds of formula I, e.g. compounds of formula IE wherein $R^{22}$ is —CH$_2$OH, by well known methods. The reaction is shown in Scheme 8:

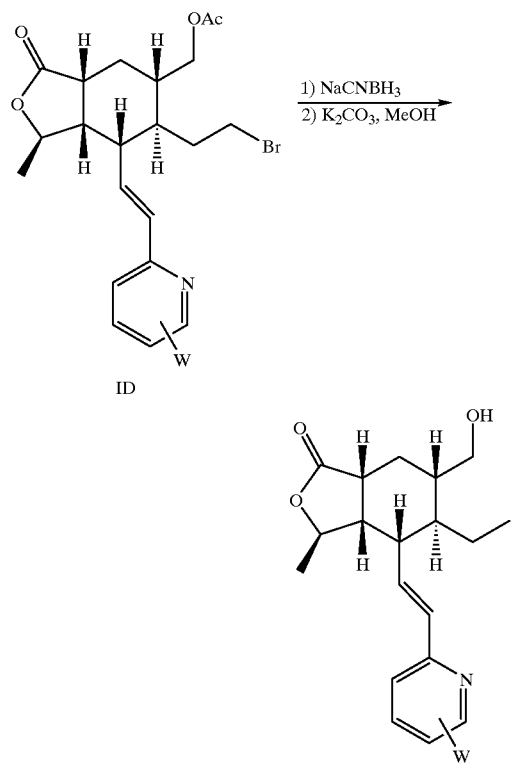

Tetrahydropyran analog 31 can be prepared starting from 3-formyl-5,6-dihydro-2H-pyran (known compound) and using the similar procedure used in Scheme 1. The ring can be opened regioselectively using BBr$_3$ and the alcohol can be protected to give the acetate ID. Bromide reduction with NaCNBH$_3$, followed by acetate deprotection, furnishes alcohol IE.

Starting materials for the above processes are either commercially available, known in the art, or prepared by procedures well known in the art.

Reactive groups not involved in the above processes can be protected during the reactions with conventional protecting groups which can be removed by standard procedures after the reaction. The following Table A shows some typical protecting groups:

TABLE A

| Group to be Protected | Group to be Protected and Protecting Group |
|---|---|
| —COOH | —COOaklyl, —COObenzyl, —COOphenyl |
| \NH/ | \NCOalkyl/, \NCObenzyl/, \NCOphenyl/, \NCH$_2$OCH$_2$CH$_2$Si(CH$_3$)$_3$/, \NC(O)OC(CH$_3$)$_3$/, \N-benzyl/, \NSi(CH$_3$)$_3$/, \NSi(CH$_3$)$_2$—C(CH$_3$)$_3$/ |
| —NH$_2$ | (N-succinimidyl) |
| —OH | —OCH$_3$, —OCH$_2$OCH$_3$, —OSi(CH$_3$)$_3$, —OSi(CH$_3$)$_2$—C(CH$_3$)$_3$ or —OCH$_2$phenyl |

The present invention also relates to a pharmaceutical composition comprising a compound of formula I of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily dose of a compound of formula I for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I. In the procedures, the following abbreviations are used: room temperature (rt), tetrahydrofuran (THF), ethyl ether (Et$_2$O), methyl (Me), ethyl (Et), ethyl acetate (EtOAc), dimethylformamide (DMF), 4-dimethylaminopyridine (DMAP), 1,8-diazabicyclo[5.4.0]undec-7-ene (DBU), 1,3-dicyclohexylcarbodiimide Preparation 1

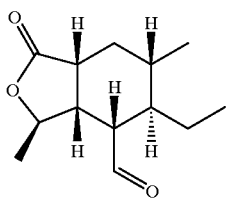

Step 1:

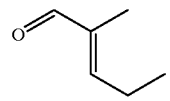

See *J. Org. Chem.*, 59 (17) (1994), p. 4789.

Step 2:

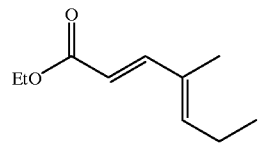

To a suspension of 60% NaH (7.42 g, 185.5 mmol, 1.3 eq) in 300 ml THF at 0° C. was added dropwise triethylphosphono acetate (37 ml, 186.5 mmol, 1.3 eq) and the mixture was stirred at 0° C. for 30 min. The product of Step 1 (14.0 g, 142.7 mmol) was added and the mixture was stirred at 0° C. for 30 min. The reaction was quenched by the addition of aq. NH$_4$Cl (500 ml), the THF was evaporated and the aqueous phase was extracted with 3×200 ml of Et$_2$O, the combined organic layer was washed with brine (300 ml), dried over MgSO$_4$, filtered and evaporated to give the crude mixture which was chromatographed (5% Et$_2$O-hexane) to give 18.38 g (77% yield) of liquid.

$^1$H NMR (400 MHz, CDCl$_3$) 7.29 (d, 1H, J=15.4), 5.86 (t, 1H, J=7.4), 5.76 (d, 1H, J=15.4), 4.18 (q, 2H, J=7.2), 2.22–2.15 (m, 2H), 1.74 (d, 3H, J=0.7), 1.27 (t, 3H, J=7.2), 1.00 (t, 3H, J=7.7) $^{13}$C NMR (100 MHz, CDCl$_3$) 167.29, 149.38, 143.45, 132.04, 115.39, 60.08, 22.14, 14.42, 13.58, 12.05 MS: 169 (MH$^+$)

Step 3:

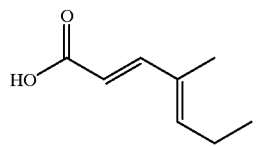

To a solution of the product of Step 2 (6.4 g, 38 mmol) in THF and MeOH (40 ml each) was added a solution of KOH (6.4 g, 114 mmol, 3 eq) in $H_2O$ (40 ml). The mixture was stirred at rt for 2 h, cooled to 0° C. and $H_2O$ (100 ml) and 1N HCl (150 ml) were added. The mixture was extracted with EtOAc (3×100 ml), the combined organic layer was washed with $H_2O$ (150 ml) and brine (150 ml), dried over $MgSO_4$, filtered and evaporated to give 5.26 g (99% yield) of crystalline solid.

$^1$H NMR (400 MHz, $CDCl_3$) 7.40 (d, 1H, J=16), 5.95 (t, 1H, J=7.2), 5.79 (d, 1H, J=16), 2.26–2.19 (m, 2H), 1.78 (s, 3H), 1.04 (t, 3H, J=7.6)

Step 4:

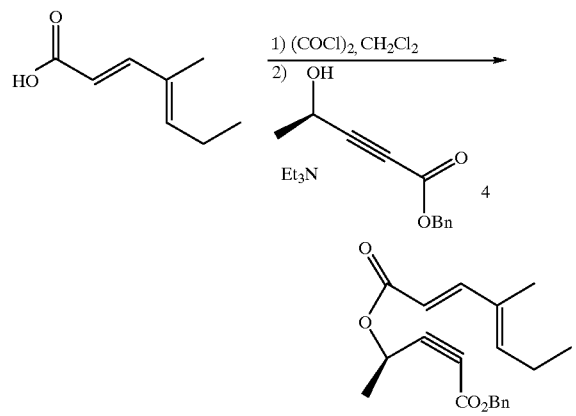

To a solution of the product of Step 3 (2.0 g, 14.3 mmol) in $CH_2Cl_2$ (70 ml) was added oxalyl chloride (2.5 ml, 28.7 mmol, 2 eq.) followed by DMF (33 μl, 3 mol %.). The mixture was stirred at rt for 1 h, then the solvent was evaporated to give the crude acid chloride which was dissolved in $CH_2Cl_2$ (70 ml) and cooled to 0° C. To this was added DMAP (175 mg, 1.43 mmol, 0.1 eq.) and a solution of alcohol 4 (2.62 g, 12.8 mmol, 0.9 eq.)in $CH_2Cl_2$ (5 ml) followed by $Et_3N$ (4 ml, 28.7 mmol, 2 eq.). The mixture was stirred at 0° C. for 2 h, diluted with $Et_2O$ (200 ml), washed with aq. $NaHCO_3$ and brine (200 ml each), and dried over $MgSO_4$. The solution was filtered, concentrated and the resultant residue was chromatographed with 5% EtOAc-hexane to provide 3.56 g (85%) of pale-yellow resin.

$^1$H NMR (400 MHz, $CDCl_3$) 7.38–7.33 (m, 6H), 5.93 (t, 1H, J=7.4), 5.77 (d, 1H, J=15.6), 5.62 (q, 1H, J=6.2), 5.20 (s, 2H), 2.25–2.18 (m, 2H), 1.76 (d, 3H, J=0.4), 1.58 (d, 3H, J=6.2), 1.03 (t, 3H, J=7.4)

Step 5:

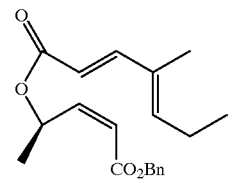

To a solution of the product of Step 4 (3.19 g, 9.8 mmol) in THF (50 ml) was added Lindlar catalyst (320 mg, 10 wt %) and quinoline (230 μl, 2.0 mmol, 0.2 eq.). The suspension was stirred under 1 atm. $H_2$ until the starting material was consumed. The solution was filtered through celite and evaporated. The resin was dissolved in EtOAc (250 ml) and washed with 1N HCl (3×100 ml) and brine (100 ml). The solution was dried over $MgSO_4$, filtered and evaporated to give 3.17 g of crude alkene which was used directly in the next step.

Step 6:

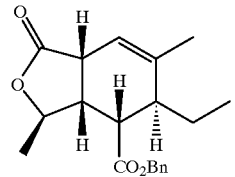

A solution of the product of Step 5 (3.15 g, 9.6 mmol) in m-xylene (100 ml) was heated at 185° C. for 10 h. The solution was cooled to rt and stirred for 1 h with DBU (290 μl, 1.94 mmol, 0.2 eq.). The solvent was evaporated and the crude was chromatographed with 10% EtOAc-hexane to provide 1.1 g (35%) of exo product. $^1$H NMR (400 MHz, $CDCl_3$) 7.38–7.34 (m, 5H), 5.45 (br s,1 H), 5.14 (ABq, J=12.0, 22.8, 2H), 4.52 (dq, J=6.1, 8.1, 1H), 3.26–3.23 (m, 1H), 2.87 (dd, J=9.4, 4.6, 1H), 2.62 (dt, J=8.1, 4.5, 1H), 2.54 (br s, 1H), 1.71 (t, J=1.2, 3H), 1.69–1.60 (m, 1H), 1.50–1.44 (m, 1H), 1.20 (d, J=6.4, 3H), 0.77 (t, J=7.4, 3H) $^{13}$C NMR (100 MHz, $CDCl_3$) 175.25, 173.04, 137.86, 135.00, 128.38, 128.34, 128.30, 116.54, 76.64, 66.70, 42.85, 42.14, 41.40, 37.27, 22.52, 21.65, 20.44, 8.98 $[\alpha]^{22}_D$=−64.4 (c 1, $CH_2Cl_2$) HRMS: 329.1754, calculated 329.1753

Step 7:

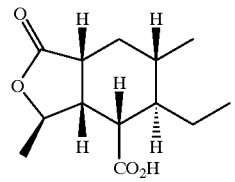

To a solution of the product of Step 6 (1.35 g, 4.1 mmol) in EtOAc (30 ml) was added 10% Pd-C (140 mg, 10 wt %) and the suspension was stirred under $H_2$ balloon for 5 h. The mixture was filtered through celite and concentrated. The crude material was dissolved in MeOH (30 ml), $PtO_2$ (100 mg) was added and the mixture was shaken in a Parr vessel at 50 Psi $H_2$ for 2 days. The mixture was filtered through celite and evaporated to give 980 mg (99%) of the acid as foam.

$^1$H NMR (400 MHz, $CDCl_3$) 4.73–4.66 (m, 1H), 2.71 (dd, J=11.8, 5.4, 1H), 2.68–2.62 (m, 1H), 2.53 (dt, J=10.0, 6.4,

1H), 1.92, ddd, J=13.4, 6.0, 2.6, 1H), 1.63–1.57 (m, 1H), 1.52–1.20 (unresolved m, 3H), 1.30(d, J=5.9, 3H), 0.96 (d, J=6.6, 3H), 0.93–0.89 (m, 1H), 0.80 (t, J=7.5, 3H) MS: 319.1 (MH+.DMSO)

Step 8:

To a solution of the product of Step 7 (490 mg, 2.04 mmol) in CH$_2$Cl$_2$ (20 ml) was added oxalyl chloride (360 µl, 4.13 mmol, 2 eq.) followed by 1 drop of DMF. The solution was stirred at rt for 1 h and the solvent was removed to provide the crude acid chloride, which was dissolved in toluene (20 ml) and cooled to 0° C. To this was added Pd(PPh$_3$)$_4$ (236 mg, 0.20 mmol, 0.1 eq.) followed by Bu$_3$SnH (825 µl, 3.07 mmol, 1.5 eq.). The mixture was stirred for 3 h at 0° C., concentrated and chromatographed with 25% EtOAc-hexane to provide the title compound 220 mg (48%) as a resin.

$^1$H NMR (400 MHz, CDCl$_3$) 9.72 (d, J=3.6, 1H), 4.70 (dq, J=5.7, 9.5, 1H), 2.71–2.64 (m, 2H), 2.56–2.51 (m, 1H), 1.98 (ddd, J=13.5, 6.1, 2.9, 1H), 1.68–1.59 (m, 3H), 1.52–1.37 (m, 1H), 1.36 (d, J=5.9, 3H), 1.32–1.20 (m, 1H), 1.00 (d, J=6.2, 3H), 0.80 (d, J=7.3, 3H)

Preparation 2

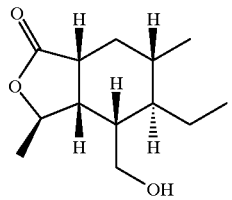

Step 1:

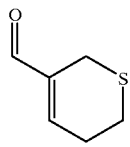

The thiopyran enal was prepared according to the procedure of McGinnis and Robinson, *J. Chem. Soc.*, 404 (1941), 407.

Step 2:

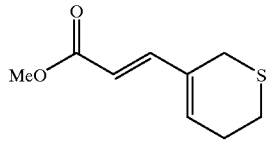

To a suspension of 60% NaH (6.3 g, 158 mmol, 1.3 eq.) in THF (200 ml) at 0° C. was added methyl diethylphosphonoacetate (29 ml, 158 mmol, 1.3 eq.) and the mixture was stirred at 0° C. for 30 min. The solution was then transferred to a solution of the product of Step 1 (15.6 g, 122 mmol) in THF (100 ml) and stirred at 0° C. for 1 h. The reaction was quenched by the addition of aq. NH$_4$Cl (500 ml) and the THF was evaporated. The aqueous phase was extracted with Et$_2$O (3×200 ml) and the combined organic layer was washed with H$_2$O and brine (200 ml each). The solution was dried over MgSO$_4$, concentrated and the resultant residue was chromatographed with 5% EtOAc-hexane to provide 13.0 g (58%) of oil. $^1$H NMR (400 MHz, CDCl$_3$) 7.26 (d, J=15.9 Hz, 1H), 6.26 (t, J=4.4 Hz, 1H), 5.78 (dd, J=15.9, 0.6 Hz, 1H), 3.75 (s, 3H), 3.25–3.23 (m, 2H), 2.71 (t, J=5.8 Hz, 2H), 2.57–2.53 (m, 2H).

Step 3:

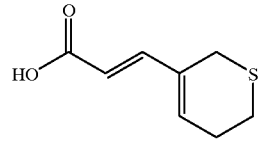

To a solution of the product of Step 2 (13.0 g, 70.6 mmol) in THF and MeOH (50 ml each) was added a solution of KOH (11.9 g, 212 mmol, 3.0 eq.) in H$_2$O (50 ml). The mixture was stirred at rt for 1 h, diluted with H$_2$O (100 ml) and acidified with 1N HCl. The aqueous phase was extracted with EtOAc (3×200 ml) and the combined organic layer was washed with H$_2$O and brine (300 ml each). The solution was dried over MgSO$_4$, filtered and evaporated to give 11.66 g (97%) of pale-yellow solid. $^1$H NMR (400 MHz, CDCl$_3$) 7.34 (d, J=15.6 Hz,1H), 6.32 (t, J=4.4 Hz,1H), 5.78 (d, J=15.6 Hz, 1H), 3.26 (d, J=1.6 Hz, 2H), 2.72 (t, J=5.8 Hz, 2H), 2.59–2.55 (m, 2H).

Step 4:

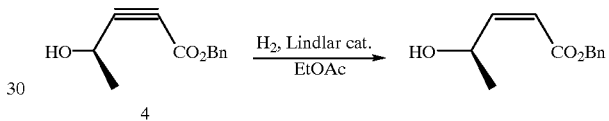

To a solution of 4 (5.2 g) in EtOAc (120 ml) was added Lindlar catalyst (520 mg) and the suspension was stirred under 1 atm. H$_2$. Another portion of catalyst (500 mg) was added after 45 min. and the mixture stirred for further 30 min. The mixture was filtered through a celite pad and evaporated to provide 5.2 g (99%) of the desired alkene. $^1$H NMR (400 MHz, CDCl$_3$) 7.38–7.26 (m, 5H), 6.32 (dd, J=11.9, 6.6 Hz, 1H), 5.86 (d, J=12.0 Hz, 1H), 5.18 (s, 2H), 5.12–5.07 (m, 1H), 3.20 (br s,1H), 1.34 (d, J=6.6 Hz, 3H).

Step 5:

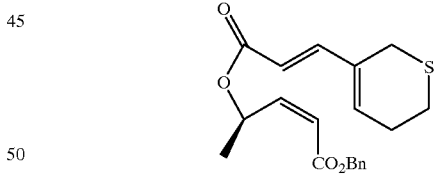

To a solution of the product of Step 3 (2.45 g, 14.39 mmol) in CH$_2$Cl$_2$ (60 ml) at 0° C. was added DCC (3.27 g, 15.85 mmol, 1.1 eq.) followed by DMAP (352 mg, 2.88 mmol, 0.2 eq.) and the mixture was stirred at 0° C. for 30 min. To this was added a solution of 3.27 g (15.85 mmol, 1.1 eq.) of the alcohol of Step 4 in 10 ml of CH$_2$Cl$_2$ and the mixture was stirred at 0° C. for 5 hr and at rt for 1 hr. The solution was diluted with 350 ml of Et$_2$O and washed with 2×200 ml of aq. citric acid, 200 ml of aq. NaHCO$_3$ and 200 ml of brine. The solution was dried over MgSO$_4$, filtered, concentrated and the resultant residue was chromatographed with 6% EtOAc-hex to provide 2.1 g (41%) of resin. $^1$H NMR (400 MHz, CDCl$_3$) 7.38–7.32 (m, 5H), 7.45 (d, J=16.0 Hz, 1H), 6.38–6.34 (m, 1H), 6.26 (t, J=4.6 Hz, 1H), 6.21 (d, J=11.6 Hz, 1H), 6.19 (d, J=11.2 Hz, 1H), 5.85 (dd, J=11.6, 1.2 Hz, 1H), 5.76 (d, J=16.0 Hz, 1H), 5.18 (d, J=1.2 Hz, 2H), 3.24 (d, J=2.0 Hz, 2H), 2.71 (t, 2H, J=5.6 Hz, 2H), 2.56–2.52 (m, 2H), 1.41 (d, J=6.4 Hz, 3H)

Step 6:

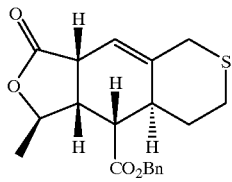

A solution of the product of Step 5 (2.1 g, 5.85 mmol) in m-xylene (50 ml) was heated at 200° C. for 6 h in sealed tube. The solution was cooled to rt and stirred with DBU (178 μl, 1.19 mmol, 0.2 eq.) for 1 h, concentrated and chromatographed with 15% EtOAc-hexane to provide 1.44 g (69%) of the desired exo product. $^1$H NMR (400 MHz, CDCl$_3$) 7.39–7.35 (m, 5H), 5.46 (br s,1H), 5.16 (ABq, J=21.6, 12.0 Hz, 2H), 4.42 (dq, J=9.2, 6.0 Hz,1H), 3.36–3.33 (m 2H), 3.08 (dd, J=14.4, 2.4 Hz,1H), 2.85 (ddd, J=13.9, 12.4, 2.5 Hz,1H), 2.72–2.57 (m, 4H), 2.27–2.21 (m,1H), 1.47–1.25 (m, 1H), 1.12 (d, J=6.4 Hz, 3H)

Step 7:

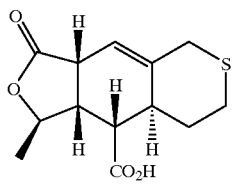

To a solution of the product of Step 6 (750 mg, 2.09 mmol) in CH$_2$Cl$_2$ (10 ml) at −78° C. was added BBr$_3$ in CH$_2$Cl$_2$ (4.2 ml of 1M solution). The solution was stirred at −78° C. for 30 min. and at 0° C. for 30 min, then poured into aq. K$_2$CO$_3$ (100 ml). The aqueous phase washed with Et$_2$O (2×50 ml) and the organic layer was back extracted with aq. K$_2$CO$_3$ (50 ml). The combined aqueous phase was acidified with 1N HCl and extracted with EtOAc (3×50 ml). The EtOAc layer was washed with brine (50 ml), dried over MgSO$_4$, filtered and evaporated to provide 500 mg (89%) of acid. $^1$H NMR (400 MHz, CDCl$_3$) 5.50 (br s, 1H), 4.47 (dq, J=9.6, 6.0 Hz, 1H), 3.43–3.39 (m, 1H), 3.36 (d, J=15.6 Hz, 1H), 3.10 (dd, J=14.0, 2.4 Hz, 1H), 2.91–2.84 (m, 1H), 2.82–2.77 (m, 1H), 2.70 (dd, J=10.6, 4.2 Hz, 1H), 2.69–2.63 (m, 1H), 2.57–2.52 (m, 1H), 2.34–2.29 (m, 1H), 1.53–1.42 (m, 1H), 1.34 (d, J=6.0 Hz, 3H).

Step 8:

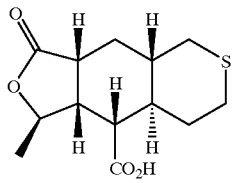

To a solution of the product of Step 7 (500 mg, 1.86 mmol) in MeOH (30 ml) was added AcOH (3 ml) and PtO$_2$ (250 mg) and the suspension was shaken under 40 Psi H$_2$ in a Parr vessel for 1.5 days. The catalyst was filtered off with a celite pad, the solution was concentrated and the resultant residue was dissolved in AcOH—MeOH—CH$_2$Cl$_2$ mixture (0.5:2:97.5 v/v/v/) and filtered through a short SiO$_2$ column to provide 400 mg (79%) of the reduced product as a resin which solidified on standing. $^1$H NMR (400 MHz, CDCl$_3$) 4.68 (dq, J=9.4, 5.9 Hz, 1H), 2.76–2.69 (m, 2H), 2.60–2.55 (m, 3H), 2.49 (d, J=11.6 Hz, 1H), 2.10 (br s, 1H), 1.93 (ddd, J=13.5, 6.0, 2.7 Hz, 1H), 1.60–1.48 (m, 2H), 1.45–1.19 (m, 3H), 1.33 (d, J=5.6 Hz, 3H).

Step 9:

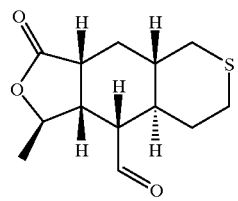

To a solution of the product of Step 8 (97 mg, 0.36 mmol) in CH$_2$Cl$_2$ (4 ml) was added oxalyl chloride (94 μl) followed by 1 drop of DMF. The solution was stirred for 1 h at rt and concentrated to provide the crude acid chloride which was dissolved in toluene (3 ml) and cooled to 0° C. Pd(PPh$_3$)$_4$ (42 mg, 0.04 mmol, 0.1 eq.) was added, followed by Bu$_3$SnH (94 μl). The mixture was stirred at 0° C. for 3 h, concentrated and chromatographed with 25% EtOAc-hexane to provide 73 mg (80%) of aldehyde as white solid. $^1$H NMR (400 MHz, CDCl$_3$) 9.75 (d, J=2.8 Hz, 1H), 4.62 (dq, J=9.7, 6.0 Hz, 1H), 2.8–2.70 (m, 2H), 2.65–2.55 (m, 3H), 2.50 (d, J=7.2 Hz), 2.10 (ddd, J=13.2, 6.4, 3.0 Hz, 1H), 1.94 (ddd, J=13.6, 6.0, 3.0, 1H), 1.69 (dq, J=10.9 Hz, 3.00 Hz, 1H), 1.58–1.48 (m, 1H), 1.42–1.20 (m, 3H), 1.33(d, J=6.4 Hz, 3H).

Step 10:

To a solution of the product of Step 9 (90 mg, 0.35 mmol) in MeOH (10 ml) (4:1 v/v) at 0° C., excess NaBH$_4$ was added and the mixture stirred for 15 min at 0° C. The reaction was quenched with aq. NH$_4$Cl (50 ml) and extracted with EtOAc (3×20 ml). The combined organic layer was washed with brine (50 ml), dried over MgSO$_4$ and concentrated to provide the crude alcohol. A solution of the alcohol in MeOH-THF (6 ml, 1:1 v/v) was added to a flask containing excess Raney nickel which was washed with dioxane and THF. The suspension was heated at reflux for 3 h, cooled, filtered, concentrated and chromatographed with 25% EtOAc-hex to provide 54 mg (67%) of title compound as a resin. $^1$H NMR (400 MHz, CDCl$_3$) 4.70 (dq, J=9.7, 5.9 Hz, 1H), 3.73 (dd, J=10.5, 3.4 Hz, 1H), 3.62 (dd, J=10.5, 7.6 Hz, 1H), 2.60–2.53 (m, 1H), 2.46 (ddd, J=9.6, 7.2, 5.2 Hz, 1H), 1.90 (ddd, J=13.5, 6.1, 3.1 Hz, 1H), 1.87–1.81 (m, 1H), 1.77 (br s, 1H), 1.66–1.59 (m, 1H), 1.50 (d, J=6.0 Hz, 3H), 1.48–1.36 (m, 2H), 1.25–1.14 (m, 2H), 0.93 (d, J=6.6 Hz, 3H), 0.78 (d, J=7.5 Hz, 3H) $^{13}$C NMR (100 MHz, CDCl$_3$) 178.58, 77.63, 61.79, 45.10, 42.49, 39.37, 38.65, 33.44, 31.96, 21.39, 19.91, 19.74, 7.26.

Preparation 3

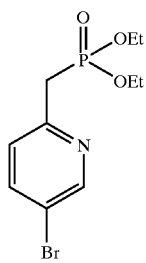

Step 1:

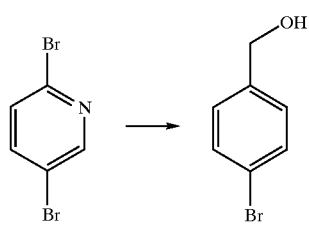

Prepared according to the procedure described in Wang et. al. *Tet. Lett*, 41, (2000), p. 4335–4338.

Step 2:

To a solution of the product of Step 1 (20 g, 106 mmol) and Et$_3$N (17.8 ml, 128 mmol, 1.2 eq.) in CH$_2$Cl$_2$ (300 ml) kept~–30° C. was slowly added CH$_3$SO$_2$Cl (9.1 ml, 118 mmol, 1.1 eq.). The slurry was stirred for 1 h while it warmed up to 0° C. The reaction mixture was diluted with aq. NaHCO$_3$ (500 ml) and the organic layer was separated. The aqueous layer was extracted with Et$_2$O (2×200 ml) and the combined organic layers was washed with aq. NaHCO$_3$ (2×300 ml) and brine (300 ml). The solution was dried over MgSO$_4$, filtered and evaporated to give the crude mesylate, which was used as such for the next step.

$^1$H NMR: 8.67 (d, J=2.0 Hz, 1H), 7.89 (dd, J=8.4, 2.4 Hz, 1H), 7.33 (d, J=8.4 Hz, 1H), 5.28 (s, 2H), 3.10 (s, 3H).

Step 3:

To a suspension of 60% NaH (8.5 g, 212 mmol 2.0 eq.) in THF (500 ml) at rt was added diethylphosphite (27.4 ml, 213 mmol, 2 eq,) drop by drop and the mixture was stirred for 1 h. To this cloudy solution was added a solution of the product of Step 2 in THF (125 ml) and the mixture was stirred at rt for 1 h. The reaction was quenched by the addition of H$_2$O (500 ml), the THF was evaporated and the aq. layer was extracted with EtOAc (4×150 ml). The combined organic layers were washed with aq. K$_2$CO$_3$ (2×300 ml), brine (300 ml), dried over MgSO$_4$, filtered, evaporated and the crude product was chromatographed with 5:95 CH$_3$OH—CH$_2$Cl$_2$ to give 31.7 g (97%) of oil.

$^1$H NMR: 8.59 (d, J=2.0 Hz,1H), 7.76 (dd, J=8.2, 2.1 Hz, 1H), 7.29 (dd, J=8.2, 2.2 Hz,1H), 4.12–4.05 (m, 4H), 3.36 (d, J=22.0 Hz, 2H), 1.27 (t, J=7.0 Hz, 6H)

Preparation 4

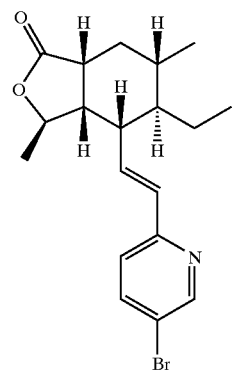

To a solution of the product of Preparation 3 (15 g, 49 mmol, 1.5 eq.) in THF (100 ml) at 0° C. was added 1M LHMDS in THF (49 ml, 49 mmol, 1.5 eq.) and the solution was stirred for 30 min. To this was added Ti(O'Pr)$_4$ (14.4 ml, 49 mmol, 1.5 eq.) followed by a solution of the product of Preparation 1 (7.3 g, 32 mmol) in THF (30 ml) and the mixture was stirred at rt for 45 min. The solution was diluted with aq. potassium sodium tartrate (300 ml) and the THF was evaporated. The slurry was extracted with EtOAc (4×100 ml) and the combined organic layer washed with brine (100 ml), dried over MgSO$_4$, filtered, concentrated and the resultant crude product was chromatographed with 15:85 EtOAc-hexane to provide 11.8 g (96%) of foam.

$^1$H NMR: 8.58 (d, J=2.4 Hz, 1H), 7.74 (dd, J=8.4, 2.8 Hz, 1H), 7.09 (d, J=8.4 Hz, 1H), 6.55 (dd, J=15.6, 10.0 Hz, 1H), 6.45 (d, J=16.0 Hz, 1H), 4.75–4.68 (m, 1H), 2.69–2.56 (m, 2H), 2.32 (dt, J=10.1, 6.5 Hz, 1H), 1.98 (ddd, J=13.4, 6.6, 2.8 Hz, 1H), 1.67–1.59 (m, 1H), 1.47–1.39 (m, 2H), 1.37 (d, J=5.9 Hz, 3H), 1.31–1.20 (m, 2H), 0.98 (d, J=6.2 Hz, 3H), 0.73 (t, J=7.5 Hz, 3H)

Preparation 5

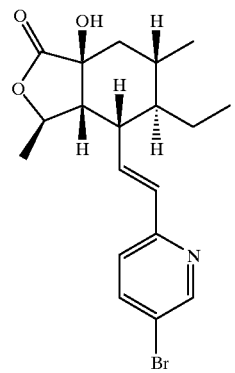

To a solution of the product of Preparation 4 (7.2 g, 19 mmol), in THF (100 ml) at –78° C. was added 1M LHMDS in THF (23 ml, 23 mmol, 1.2 eq.). The solution was stirred for 30 min at –78° C., 30 min at 0° C. and cooled back to –78° C. To this was added a solution of (1S)-(+)-(10-camphorsulfonyl)oxaziridine (6.0 g, 26 mmol, 1.4 eq.) in THF (50 ml) and the mixture was stirred for 1 h at –78° C. and 1.5 h at 0° C. To the solution was added aq. NH$_4$Cl (300 ml), THF was evaporated and the aqueous layer was extracted with EtOAc (4×100 ml). The combined organic layer was washed with brine (100 ml), dried over MgSO$_4$, filtered, concentrated and the crude product was chromatographed with 15:20:65 EtOAc—CH$_2$Cl$_2$-hex to provide 6.4 g (85%) of foam.

$^1$H NMR: 8.56 (d, J=2.0 Hz, 1H), 7.72 (dd, J=8.4 Hz, 1H), 7.07 (d, J=8.4 Hz, 1H), 6.56 (dd, J=15.6, 9.8 Hz, 1H), 6.48 (d, J=15.6 Hz, 1H), 4.62–4.55 (m, 1H), 3.72 (br s, 1H), 2.80–2.74 (m, 1H), 2.28 (dd, J=9.6, 5.6 Hz, 1H), 1.81–1.78 (m, 2H), 1.63–1.58 (m, 1H), 1.44–1.27 (m, 3H), 1.37 (d, J=6.0 Hz, 3H), 0.94 (d, J=6.4 Hz, 3H), 0.73 (t, J=7.5 Hz, 3H)

Preparation 6

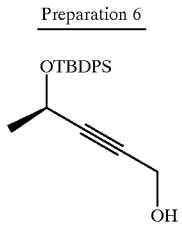

Step 1:

To a solution of (R)-(+)-3-butyn-2-ol (5 ml, 64 mmol) in CH$_2$Cl$_2$ (100 ml) at rt was added DMAP (780 mg, 6.4 mmol, 0.1 eq.), tert-butylchlorodiphenylsilane (17.4 ml, 67 mmol, 1.05 eq.) and Et$_3$N (9.8 ml, 70 mmol, 1.1 eq.). The mixture was stirred overnight, diluted with Et$_2$O (400 ml), washed with 1N HCl (2×200 ml), aq. NaHCO$_3$ (200 ml), brine (200 ml), dried over MgSO$_4$, filtered and evaporated to give ~20 g of oil which was used as such for the next step.

Step 2:

To a solution of the product of Step 1 in THF (200 ml) at −78° C. was added 2.5M BuLi in hexanes (30.4 ml, 76 mmol, 1.1 eq.), the solution was stirred for 1 h and solid paraformaldehyde (4.15 g, 138 mmol, 2.0 eq.) was added. The mixture was stirred for 15 min at −78° C., 1 h at rt, then quenched with the addition of aq. NH$_4$Cl (500 ml). The THF was evaporated and the aqueous layer was extracted with EtOAc (3×200 ml). The combined organic layers were washed with H$_2$O (2×300 ml) and brine (300 ml), dried over MgSO$_4$, filtered, evaporated and the crude was chromatographed with 10% EtOAc-hex to provide 16.5 g (71%) of resin.

$^1$H NMR: 7.77–7.74 (m, 2H), 7.71–7.68 (m, 2H), 7.46–7.36 (m, 6H), 4.53 (tq, J=1.8, 6.5 Hz, 1H), 4.08 (dd, J=6.2, 1.8 Hz), 2.82 (d, J=6.4 Hz, 3H), 1.07 (s, 9H)

EXAMPLE 1

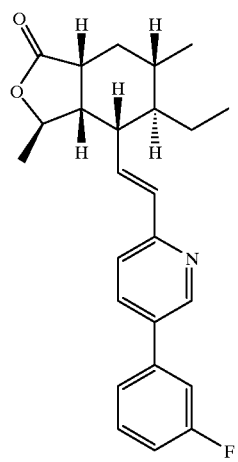

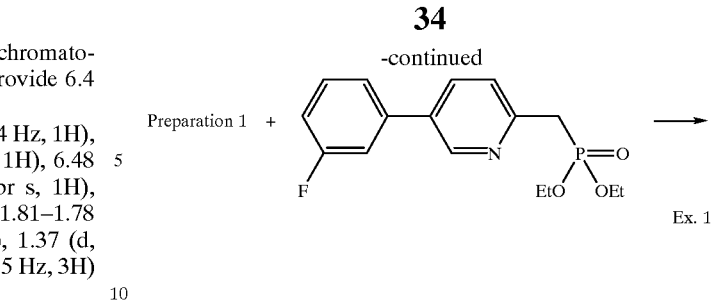

Ex. 1

To a solution of the phosphonate (650 mg, 2.01 mmol, 2 eq.) in THF (8 ml) at 0° C. was added BuLi in hexanes (790 μl of 2.5M solution, 2.0 mmol, 2 eq.), the mixture was stirred for 10 min, then Ti(O$^i$Pr)$_4$ (590 μl, 2.0 mmol, 2 eq.) was added and the solution was stirred at rt for 10 min. To this was added a solution of the product of Preparation 1 (220 mg, 0.98 mmol) in THF (3 ml) and the mixture was stirred at rt for 1.5 h. To the solution was added aq. Rochelles's salt (100 ml) and THF was evaporated. The aqueous phase was extracted with EtOAc (3×30 ml) and the combined organic layer was washed with brine (50 ml). The solution was dried over MgSO$_4$, concentrated and the resultant residue was chromatographed with 20% EtOAc-hexane to provide the title compound (240 mg, 62%) as a resin.

$^1$H NMR (400 MHz, CDCl$_3$) 8.78 (d, J=2.0, 1H), 7.82 (dd, J=2.4, 8.0, 1H), 7.44 (dt, J=5.7, 8.1, 1H), 7.36 (dt, J=1.2, 7.7, 1H), 7.30–7.25 (m, 2H), 7.09 (ddt, J=2.5, 1.0, 8.4, 1H), 6.61 (dd, J=15.3, 8.6, 1H), 6.56 (d, J=15.3, 1H), 4.78–4.71 (m, 1H), 2.71–2.61 (m, 2H), 2.36 (dt, J=10.0, 6.4, 1H), 1.99 ( (ddd, J=13.5, 6.1, 2.9, 1H), 1.68–1.61 (m, 1H), 1.51–1.44 (m, 2H), 1.42 (d, J=5.9, 3H), 1.39–1.22 (m, 2H), 0.99 (d, J=6.6, 3H), 0.76 (t, J=7.5, 3H) FAB HRMS: 394.2184, calculated: 394.2182 Anal. calc'd for C$_{25}$H$_{28}$FNO$_2$.HCl: C, 69.84; H, 6.80; N, 3.26. Found: C, 71.00,H, 6.96; N, 3.19.

Using a similar procedure with the appropriate phosphonate, the following compound 1A was prepared:

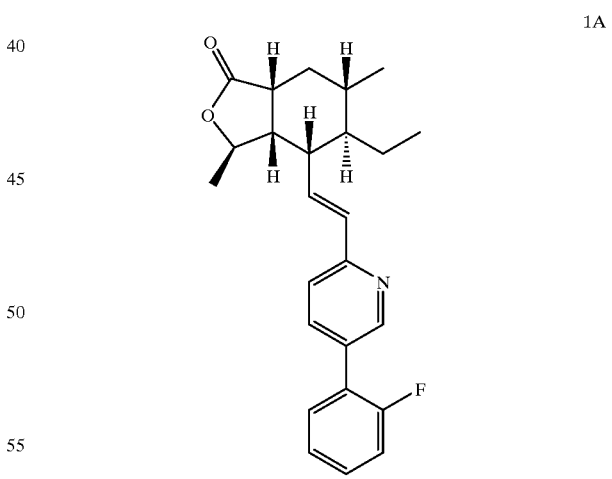

1A $^1$H NMR (400 MHz, CDCl$_3$) 8.73 (bs, 1H), 7.84 (dt, J=2.0, 8.0, 1H), 7.44 (dt, J=1.7, 7.7, 1H), 7.40–7.34 (m, 1H), 7.30 (d, J=8.0, 1H), 7.25 (dt, J=7.6, 1.1, 1H), 7.18 (ddd, J=10.6, 8.4, 1.2, 1H), 6.62 (dd, J=15.1, 8.6, 1H), 6.56 (d, J=15.1, 1H), 4.79–4.72 (m, 1H), 2.71–2.61 (m, 2H), 2.36 (dt, J=10.0, 6.5, 1H), 1.99 (ddd, J=13.5, 6.1, 2.9, 1H), 1.70–1.57 (m, 1H), 1.51–1.44 (m, 2H), 1.42 (d, J=5.9, 3H), 1.39–1.22 (m, 2H), 0.99 (d, J=6.6, 3H), 0.76 (t, J=7.3, 3H) FAB HRMS: 394.2184, calculated: 394.2182.

EXAMPLE 2

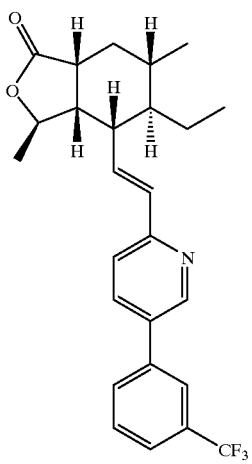

Preparation 2 +

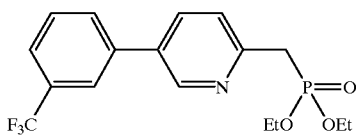

→ Ex. 2

To a solution of the product of Preparation 2 (50 mg, 0.22 mmol) in CH$_2$Cl$_2$ (3 ml) was added NMO (78 mg, 0.67 mmol, 3 eq.) and 4 A° molecular sieves (about 50 mg). After stirring for 10 min., TPAP (8 mg, 0.02 mmol, 0.1 eq.) was added and the stirring was continued for another 40 min. The mixture was diluted with Et$_2$O (20 ml), filtered through celite and concentrated to provide a residue. The residue was filtered through a short SiO$_2$ plug, eluting with 30% EtOAc-hexane to provide 38 mg of aldehyde.

In another flask containing the phosphonate (210 mg, 0.56 mmol, 3.3 eq.) in THF (1.5 ml) at 0° C. was added a 2.M solution of BuLi in hexanes (224 μl, 0.56 mmol, 3.3 eq.) and the mixture was stirred for 20 min. A solution of the above aldehyde in 1.5 ml of THF was added and the mixture was stirred at 0° C. for 1 h. The solution was diluted with EtOAc (20 ml), washed with H$_2$O (2×20 ml) and brine (20 ml), dried over MgSO$_4$, filtered, concentrated and purified by preparative TLC using 25% EtOAc-hexane to provide 9 mg of the title compound. $^1$H NMR (400 MHz, CDCl$_3$) 8.79 (d, J=2.4 Hz, 1H), 7.85 (dd, J=8.4, 2.6 Hz, 1H), 7.81 br s,1H), 7.76 (d, J=7.2 Hz, 1H), 7.67–7.58 (m, 2H), 7.31 (d, J=7.6 Hz, 1H), 6.63 (dd, J=15.6, 9.2 Hz, 1H), 6.57 (d, J=15.6 Hz, 1H), 4.79–4.72 (m, 1H), 2.71–2.61 (m, 2H), 2.37 (dt, J=10.0, 6.4 Hz, 1H), 2.00 (ddd, J=13.5, 6.3, 2.7 Hz, 1H), 1.64–1.56 (m, 1H), 1.51–1.23 (m 4H), 1.42 (d, J=6.2 Hz, 3H), 1.00 (d, J=6.6 Hz, 3H), 0.77 (t, J=7.5 Hz, 3H) FABHRMS: 446.2306 (MH$^+$), Calculated 446.2280.

Using similar procedures, the following compounds were also prepared:

EXAMPLE 3

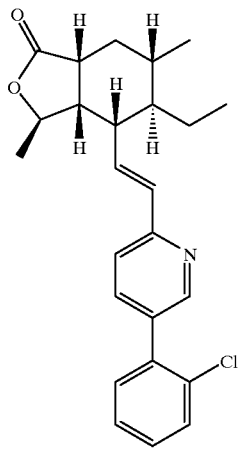

$^1$H NMR (400 MHz, CDCl$_3$) 8.62 (d, J=2.0 Hz, 1H), 7.76 (dd, J=8.0, 2.4 Hz, 1H), 7.51–7.48 (m, 1H), 7.37–7.26 (m, 4H), 6.65–6.55 (m, 2H), 4.78–4.71 (m, 1H), 2.71–2.61 (m, 2H), 2.36 (dt, J=10.0, 6.4 Hz, 1H), 1.99 (ddd, J=13.7, 6.3, 2.9 Hz, 1H), 1.68–1.61 (m, 1H), 1.50–1.45 (m, 2H), 1.43 (d, J=5.6 Hz, 3H), 1.33–1.25 (m, 2H), 0.99 (d, J=6.4 Hz, 3H), 0.76 (t, J=7.4 Hz, 3H) [α]$^{20}_D$=+13.2°(c 0.5, MeOH); FAB HRMS: 410.1891 (MH$^+$), Calculated 410.1887

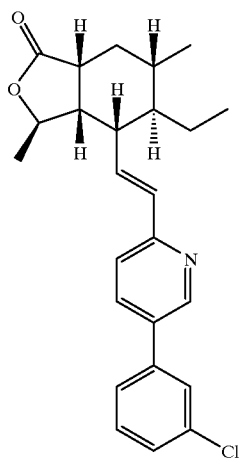

EXAMPLE 4

$^1$H NMR (400 MHz, CDCl$_3$) 8.75 (d, J=2.0 Hz, 1H), 7.80 (dd, J=8.2, 2.0 Hz, 1H), 7.54 br s, 1H), 7.46–7.34 (m, 3H), 7.29 (d, J=8.0 Hz, 1H), 6.61 (dd, J=15.3, 9.0 Hz, 1H), 6.56 (d, J=15.3 Hz, 1H), 4.78–4.71 (m, 1H), 2.70–2.60 (m, 2H), 2.31 (dt, J=10.1, 6.5 Hz, 1H), 1.98 (ddd, J=13.5, 6.4, 2.9 Hz, 1H), 1.71–1.64 (m, 1H), 1.49–1.43 (m, 2H), 1.40 (d, J=6.0 Hz, 3H), 1.33–1.21 (m, 2H), 0.99 (d, J=6.4 Hz, 3H), 0.75 (t, J=7.4 Hz, 3H) <76504-097-A-H in 2A>[α]$^{20}_D$=+23.1°(c 0.5, MeOH) FAB HRMS: 410.1887 (MH$^+$), Calculated 410.1887

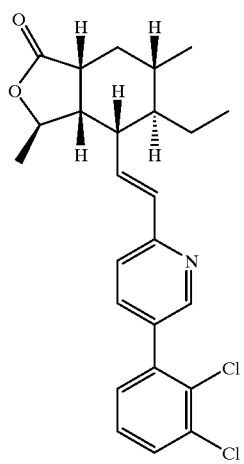

EXAMPLE 5

$^{1}$H NMR (400 MHz, CDCl$_3$) 8.58 (d, J=2.0 Hz, 1H), 7.72 (dd, J=8.0, 2.0 Hz, 1H), 7.50 (dd, J=8.0, 1.6 Hz,1H), 7.31–7.21 (m, 3H), 6.63 (dd, J=15.5, 8.8 Hz, 1H), 6.57 (d, J=15.5 Hz, 1H), 4.78–4.71 (m, 1H), 2.71–2.61 (m, 2H), 2.36 (dt, J=10.0, 6.4 Hz, 1H), 1.99 (ddd, J=13.6, 6.4, 2.8 Hz, 1H), 1.68–1.61 (m, 1H), 1.50–1.45 (m, 2H), 1.43 (d, J=6.0 Hz, 3H), 1.35–1.22 (m, 2H), 0.99 (d, J=6.4 Hz, 3H), 0.76 (t, J=7.4 Hz, 3H) [α]$^{20}_D$=+5.8°(c 0.4, MeOH) FAB HRMS: 444.1491 (MH$^+$), Calculated 444.1497.

EXAMPLE 6

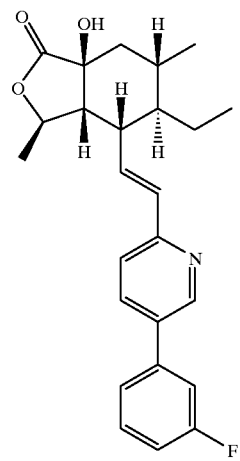

To a solution of the product of Example 1 (540 mg,1.37 mmol) in THF (8 ml) at −78° C. was added 1M LHMDS solution in THF (1.65 ml, 1.65 mmol, 1.2 eq.). The solution was stirred at −78° C. for 15 min. and at 0° C. for 30 min. It was cooled back to −78° C. and a solution of (1S)-(+)-(10-camphorsulfonyl)oxaziridine (475 mg, 2.10 mmol, 1.5 eq.) in THF (4 ml) was added. The mixture was stirred at −78° C. for 15 min. then allowed to warm up slowly to rt. To the mixture was added aq. NH$_4$Cl (100 ml) and it was then extracted with EtOAc (3×30 ml). The combined organic layer was washed with 30 ml brine, dried over MgSO$_4$, concentrated and chromatographed with 15:20:65 EtOAc—CH$_2$Cl$_2$-hexanes to provide 390 mg (69%) of resin.

$^{1}$H NMR: 8.78 (d, J=2.4 Hz, 1H), 7.82 (dd, J=8.2, 2.6 Hz, 1H), 7.44 (dt, J=6.0, 8.0 Hz, 1H), 7.37–7.35 (m, 1H), 7.29–7.25 (m, 2H), 7.09 (ddt, J=1.0, 2.4, 8.3 Hz, 1H), 6.67–6.58 (m, 2H), 4.67–4.60 (m,1H), 2.85–2.79 (m, 2H), 2.32 (dq, J=1.5, 5.7 Hz, 1H), 1.89–1.82 (m, 1H), 1.79–1.75 (m, 1H), 1.70–1.61 (m, 2H), 1.54–1.46 (m, 1H), 1.45 (d, J=6.0 Hz, 3H), 1.43–1.32 (m, 1H), 0.99 (d, J=6.6 Hz, 3H), 0.78 (t, J=7.5 Hz, 3H).

The Suzuki coupling procedure is exemplified by heating a solution of a bromide of Preparation 4 or 5 with boronic acid (1.0 to 2.0 eq.), K$_2$CO$_3$ (4 eq.) and Pd(PPh$_3$)$_4$ (5 to 10 mol %) in toluene:EtOH:H$_2$O (4:2:1, v/v/v) at 100° C. until the reaction is complete. The reaction mixture is diluted with H$_2$O, extracted with EtOAc, and the organic layer is washed with brine, dried over MgSO$_4$, filtered, concentrated and purified by chromatography to provide the desired compounds.

Using the Suzuki coupling procedure described above, the following compounds were prepared:

EXAMPLE 7

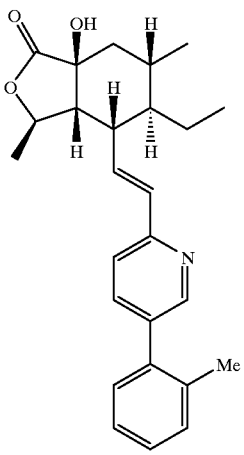

$^{1}$H NMR: 8.54 (dd, J=2.2, 0.6 Hz, 1H), 7.62 (dd, J=8.0, 2.2 Hz, 1H), 7.31–7.25 (m, 4H), 7.22–7.20 (m, 1H), 6.65–6.56 (m, 1H), 4.67–4.60 (m, 1H), 3.20 (br s,1H), 2.89–2.80 (m, 1H), 2.34 (ddd, J=10.1, 5.7, 1.5 Hz, 1H), 2.30 (s, 3H), 1.91–1.77 (m, 2H), 1.70–1.64 (m, 1H), 1.55–1.43 (m, 2H), 1.45 (d, J=6.0 Hz, 3H), 1.39–1.25 (m, 1H), 0.98 (d, J=6.50, 3H), 0.79 (t, J=7.5 Hz, 3H)

EXAMPLE 8

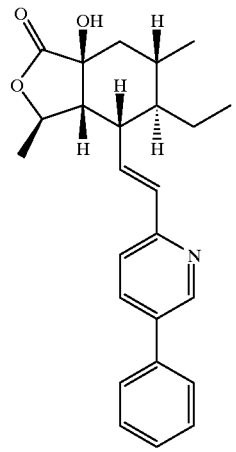

$^{1}$H NMR: 8.80 (d, J=2.0 Hz, 1H), 7.84 (dd, J=8.2, 2.2 Hz, 1H), 7.58 (d, J=7.6 Hz, 2H), 7.47 (t, J=7.4 Hz, 2H), 7.39 (t,

J=7.2 Hz, 1H), 7.29 (d, J=8.0 Hz, 1H), 6.65–6.55 (m, 2H), 4.67–4.60 (m, 1H), 3.56 (br s, 1H), 2.87–2.81 (m, 1H), 2.34 (dd, J=9.6, 5.6 Hz, 1H), 1.87–1.80 (m, 2H), 1.70–1.63 (m, 1H), 1.53–1.33 (m, 3H), 1.44 (d, J=6.0 Hz, 3H), 0.98 (d, J=6.5 Hz, 3H), 0.79 (t, J=7.4 Hz, 3H).

Also using the Suzuki coupling procedure with the appropriate reagents, compounds of the following structures were prepared:

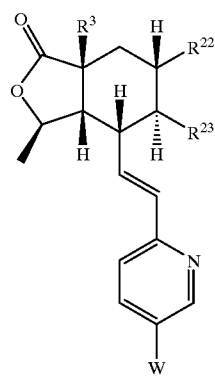

wherein $R^3$, $R^{22}$, $R^{23}$ and W are as defined in the following table (Me is methyl, Et is ethyl and Ph is phenyl):

| Ex. | $R^3$ | $R^{22}$ | $R^{23}$ | W | Analytical Data |
|---|---|---|---|---|---|
| 8B | H | Me | Et | 3-CF₃-phenyl | HRMS (MH⁺) 444.2165 |
| 8C | H | Me | Et | 3-F-phenyl | HRMS (MH⁺) 394.2184 |
| 8D | H | Me | Et | 2-F-phenyl | HRMS (MH⁺) 394.2184 |
| 8E | H | Me | Et | 2-Cl-phenyl | HRMS (MH⁺) 410.1891 |
| 8F | H | Me | Et | 3-Cl-phenyl | HRMS (MH⁺) 410.1887 |
| 8G | H | Me | Et | 2,3-diCl-phenyl | HRMS (MH⁺) 444.1491 |
| 8H | H | H | Ph | 3-F-phenyl | HRMS (MH⁺) 428.2026 |
| 8I | H | H | Ph | 2-F-phenyl | HRMS (MH⁺) 428.2027 |
| 8J | H | Me | Et | 3-acetyl-phenyl | HRMS (MH⁺) 418.2381 |
| 8K | H | Me | Et | 3-(C(=NOH)Me)-phenyl | HRMS (MH⁺) 433.2490 |
| 8L | H | Me | Et | 3-(C(=NOMe)Me)-phenyl | HRMS (MH⁺) 447.2648 |
| 8M | H | Me | Et | 3-(NHSO₂Et)-phenyl | HRMS (MH⁺) 483.2319 |
| 8N | H | Me | Et | 2-Me-phenyl | HRMS (MH⁺) 390.2441 |

-continued
| Ex. | R³ | R²² | R²³ | W | Analytical Data |
|---|---|---|---|---|---|
| 8O | H | Me | Et | 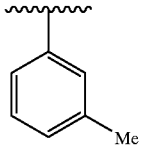 | HRMS (MH⁺) 390.2437 |
| 8P | H | Me | Et | 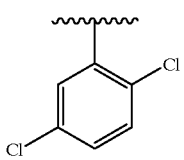 | HRMS (MH⁺) 444.1490 |
| 8Q | Me | Me | Et | 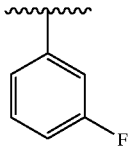 | HRMS (MH⁺) 408.2346 |
| 8R | OH | Me | Et | 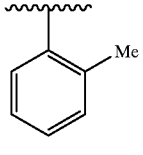 | HRMS (MH⁺) 406.2380 |
| 8S | OH | Me | Et | 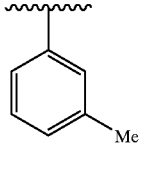 | HRMS (MH⁺) 406.2376 |
| 8T | OH | Me | Et |  | HRMS (MH⁺) 398.1788 |
| 8U | OH | Me | Et | 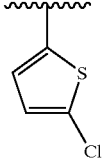 | HRMS (MH⁺) 432.1392 |
| 8V | OH | Me | Et | 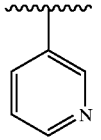 | HRMS (MH⁺) 393.2181 |
| 8W | OH | Me | Et | 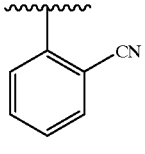 | HRMS (MH⁺) 417.2178 |
-continued
| Ex. | R³ | R²² | R²³ | W | Analytical Data |
|---|---|---|---|---|---|
| 8X | OH | Me | Et | 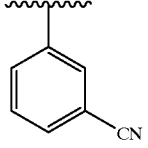 | HRMS (MH⁺) 417.2178 |
| 8Z | OH | Me | Et | 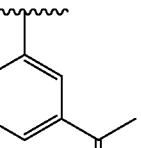 | HRMS (MH⁺) 434.2330 |
| 8AA | OH | Me | Et | 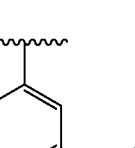 | HRMS (MH⁺) 449.2440 |
| 8AB | OH | Me | Et | 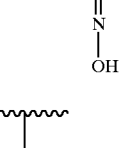 | HRMS (MH⁺) 463.2599 |
| 8AC | OH | Me | Et | 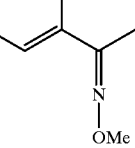 | HRMS (MH⁺) 435.2275 |
| 8AD | OH | Me | Et | 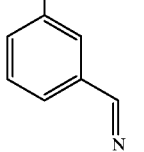 | HRMS (MH⁺) 449.2446 |
| 8AE | OH | Me | Et | 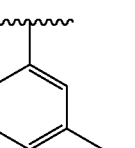 | HRMS (MH⁺) 435.2279 |

-continued
| Ex. | R³ | R²² | R²³ | W | Analytical Data |
|---|---|---|---|---|---|
| 8AF | OH | Me | Et | 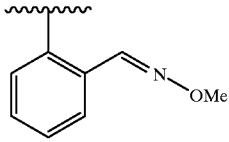 | HRMS (MH⁺) 449.2442 |
| 8AG | OH | Me | Et | 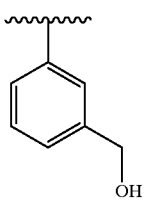 | HRMS (MH⁺) 422.2332 |
| 8AH | OH | Me | Et | 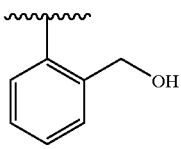 | HRMS (MH⁺) 422.2332 |
| 8AI | H | H | Et | 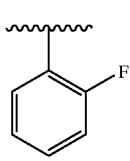 | HRMS (MH⁺) 380.2028 |
| 8AJ | H | Ph | Me | 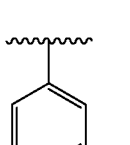 | MS(MH⁺) 442.1 |
| 8AK | H | Ph | Me | 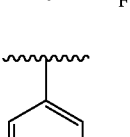 | MS(MH⁺) 458.1 |
| 8AL | OH | Me | Et | 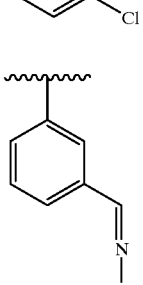 | HRMS (MH⁺) 463.2589 |
| 8AM | OH | Me | Et | 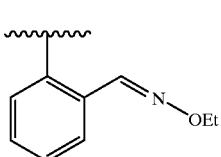 | HRMS (MH⁺) 463.2593 |
-continued
| Ex. | R³ | R²² | R²³ | W | Analytical Data |
|---|---|---|---|---|---|
| 8AN | OH | Me | Et | 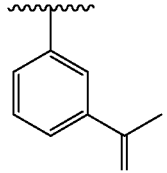 | HRMS (MH⁺) 477.2750 |
| 8AO | OH | Me | Et | 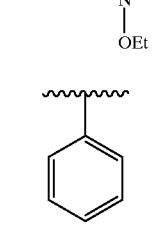 | HRMS (MH⁺) 392.2227 |
| 8AP | OH | Me | Et | 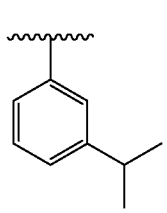 | HRMS (MH⁺) 434.2695 |
| 8AQ | OH | Me | Et | 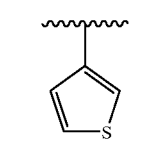 | HRMS (MH⁺) 398.1788 |
| 8AR | OH | Me | Et | 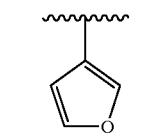 | HRMS (MH⁺) 382.2020 |
| 8AS | OH | Me | Et | 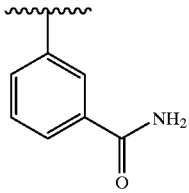 | HRMS (MH⁺) 435.2282 |
| 8AT | OH | Me | Et | 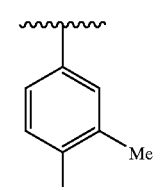 | HRMS (MH⁺) 424.0945 |
| 8AU | OMe | Me | Et | 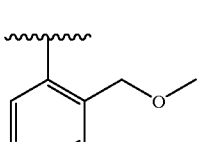 | MS(MH⁺) 450.1 |

-continued

| Ex. | R³ | R²² | R²³ | W | Analytical Data |
|---|---|---|---|---|---|
| 8AV | OH | Me | Et | 2-(methoxymethyl)phenyl | MS(MH⁺) 436.1 |
| 8AW | OMe | Me | Et | 2-(hydroxymethyl)phenyl | MS(MH⁺) 436.1 |
| 8AX | OH | Me | Et | 2-((2-methoxyethoxy)methyl)phenyl | HRMS (MH⁺) 480.2752 |
| 8AY | OH | Me | Et | 3-(1-hydroxyethyl)phenyl | HRMS (MH⁺) 436.2489 |
| 8AZ | OH | Me | Et | 2-acetylphenyl | HRMS (MH⁺) 434.2325 |
| 8BA | OH | Me | Et | 2-(1-hydroxyethyl)phenyl | HRMS (MH⁺) 436.2489 |
| 8BB | OH | H | Et | 2-methylphenyl | MS(MH⁺) 392.2 |
| 8BC | OH | H | Et | 3-fluorophenyl | MS(MH⁺) 396.3 |

-continued

| Ex. | R³ | R²² | R²³ | W | Analytical Data |
|---|---|---|---|---|---|
| 8BD | OH | H | Et | furan-3-yl | MS(MH⁺) 368.4 |
| 8BE | OH | Me | Et | 4-hydroxyphenyl | HRMS (MH⁺) 408.2169 |
| 8BF | OH | Me | Et | 5-chloro-2-methoxyphenyl | HRMS (MH⁺) 456.1941 |
| 8BG | OH | H | Me | 3-fluorophenyl | HRMS (MH⁺) 382.1813 |
| 8BH | OH | H | Me | 3-cyanophenyl | HRMS (MH⁺) 389.1863 |
| 8BI | OH | H | Me | pyridin-3-yl | HRMS (MH⁺) 365.1871 |
| 8BJ | OH | Me | Et | 5-fluoro-2-methoxyphenyl | HRMS (MH⁺) 440.2243 |
| 8BK | OH | H | Me | 2-methylphenyl | HRMS (MH⁺) 378.2064 |
| 8BL | OH | H | Me | phenyl | HRMS (MH⁺) 364.1919 |

-continued

| Ex. | R³ | R²² | R²³ | W | Analytical Data |
|---|---|---|---|---|---|
| 8BM | OH | Me | Et | (2-acetophenone oxime, =N-OH) | HRMS (MH⁺) 449.2435 |
| 8BN | OH | Me | Et | (2-acetophenone O-methyl oxime, =N-OMe) | HRMS (MH⁺) 463.2604 |
| 8BO | OH | Me | Et | (2-acetophenone O-ethyl oxime, =N-OEt) | HRMS (MH⁺) 477.2751 |
| 8BP | OH | Me | Et | (3-(2-hydroxypropan-2-yl)phenyl) | HRMS (MH⁺) 450.2640 |

EXAMPLE 9

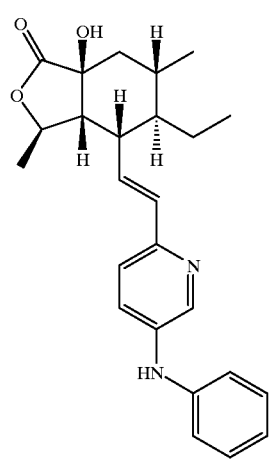

To the product of Preparation 5 (0.127 mmol) in dry toluene (5 ml) was added aniline (0.254 mmol, 2 eq.), potassium phosphate (0.380 mmol, 3 eq.), palladium acetate (6.5 mol %) and 2-(dicyclohexylphosphino)biphenyl (13 mol %). The mixture was bubbled with N₂ for 2 min. then heated to 120° C. in a sealed tube. After 16 h, the reaction was cooled to rt, poured into water and extracted with Et₂O (3×). The combined extracts were washed with brine, dried with MgSO₄, filtered and evaporated to dryness. Purification by flash chromatography (2–5% CH₃OH in CH₂Cl₂) yielded the desired product in a 66% yield ¹H NMR: 8.31 (d, J=2.8 Hz, 1H), 7.40 (dd, J=2.8, 8.5 Hz, 1H), 7.30–7.26 (m, 2H), 7.15 (d, J=8.5 Hz, 1H), 7.07 (dd, J=0.9, 8.5 Hz, 1H), 6.97 (t, J=7.4 Hz, 1H), 6.50 (d, J=15.6 Hz, 1H), 6.25 (dd, J=10.4, 15.6 Hz, 1H), 6.14 (s, 1H), 4.60–4.56 (m, 1H), 4.43 (br s,1H), 2.79–2.76 (m, 1H), 2.31 (dd, J=5.6, 9.2 Hz, 1H), 1.91–1.79 (m, 2H), 1.65–1.58 (m, 1H), 1.41–1.35 (m, 2H), 1.39 (d, J=6.0 Hz, 3H), 1.31–1.25 (m, 1H), 0.95 (d, J=6.4 Hz, 3H), 0.77 (t, J=7.4 Hz, 3H)

Using a similar procedure, compounds of the formula

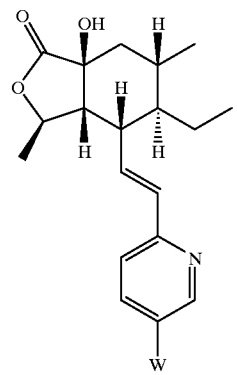

were prepared, wherein W is as defined in the table:

| Ex. | W | Analytical Data |
|---|---|---|
| 9A | (pyrrolidin-1-yl) | HRMS (MH⁺) 385.2490 |
| 9B | ((S)-2-(hydroxymethyl)pyrrolidin-1-yl) | HRMS (MH⁺) 415.2601 |
| 9C | ((R)-2-(hydroxymethyl)pyrrolidin-1-yl) | HRMS (MH⁺) 414.2593 |
| 9D | (2-oxopyrrolidin-1-yl) | HRMS (MH⁺) 399.2278 |

EXAMPLE 10

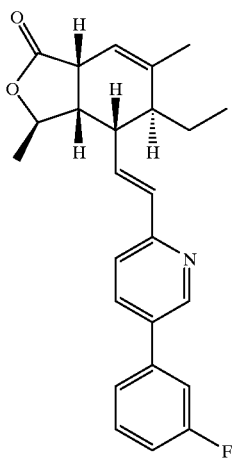

Steps 1–3:

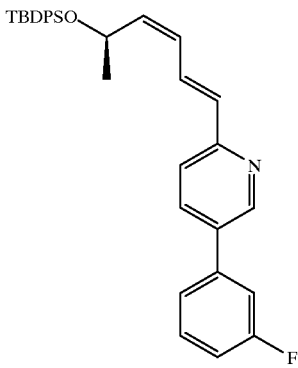

Step 1: A suspension of the alkyne of Preparation 6 (3.1 g, 9.2 mmol), quinoline (215 µl, 1.8 mmol, 0.2 eq.), and Lindlar catalyst (310 mg, 10 wt %) in EtOAc (50 ml) was stirred under 1 atm. $H_2$ (balloon) and the reaction was monitored by NMR. After the reaction was completed, it was filtered through a celite pad, washed with 1N HCl and brine, dried over $MgSO_4$, filtered and evaporated to give ~3.4 g of resin which was used as such for the next step.

Step 2: Dess-Martin reagent (4.28 g, 10.1 mmol, 1.1 eq.) was added to a mixture of the product of Step 1 and $NaHCO_3$ (1.54 g, 18.3 mmol, 2 eq.) in $CH_2Cl_2$ (30 ml) at rt and stirred for 1 hr. The mixture was diluted with $Et_2O$ (60 ml) and a solution of $Na_2S_2O_3 \cdot 5H_2O$ (4.55 g, 18.3 mmol, 2 eq.) and $NaHCO_3$ (1.54 g, 18.3 mmol, 2 eq.) in $H_2O$ (100 ml) and stirred vigorously until the two layers became clear. The organic layer was separated and the aq. layer was extracted with $Et_2O$ (2×50 ml). The combined organic layers were washed with aq. $Na_2S_2O_3/NaHCO_3$ solution (100 ml), brine (100 ml), dried over $MgSO_4$, filtered and evaporated to give ~3.5 g of aldehyde, which was used as such for the next step.

Step 3:
To a solution of a phosphonate of the formula

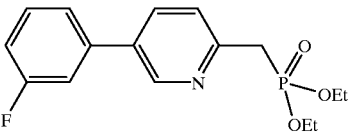

(3.9 g, 12.1 mmol, 1.3 eq.) in THF (30 ml) at 0° C. was added 60% NaH in mineral oil (480 mg, 12.0 mmol, 1.3 eq.) and the mixture was stirred for 20 min. To this was added a solution of the product of Step 2 in THF (15 ml), and after 1 hr of stirring at 0° C., it was diluted with aq. $NH_4Cl$ (200 ml). The THF was evaporated and the aq. layer was extracted with EtOAc (3×75 ml). The combined organic layers were washed with brine (100 ml), dried over $MgSO_4$, filtered, evaporated and the residue was chromatographed with 5% EtOAc-hex to provide 4.0 g (87%) of resin.

$^1$H NMR: 8.75 (d, J=2.0 Hz, 1H), 7.76 (dd, J=8.0, 2.4 Hz, 1H), 7.73–7.66 (m, 4H), 7.47–7.26 (m, 9H), 7.19 (d, J=8.0 Hz, 1H), 7.09 (ddt, J=1.1, 2.5, 8.4 Hz, 1H), 7.00 (ddd, J=15.3, 11.5, 1.1 Hz, 1H), 6.52 (d, J=15.2 Hz, 1H), 6.05–5.99 (m, 1H), 5.74–5.69 (m, 1H), 4.93–4.86 (m, 1H), 1.28 (d, J=6.4 Hz, 3H), 1.06 (s, 3H)

Step 4:

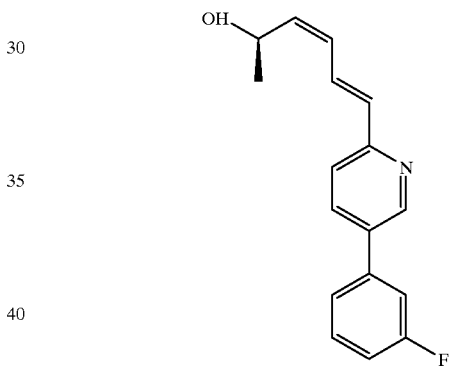

To a solution of silyl ether (4.0 g, 7.88 mmol) in THF (30 ml) at 0° C. was added 1M TBAF in THF (11.8 ml, 11.8 mmol, 1.5 eq.) and the mixture was stirred at rt for 6 h. It was diluted with aq. $NH_4Cl$ (150 ml), the THF was evaporated and the aq. layer was extracted with EtOAc (3×60 ml). The combined organic layers were washed with $H_2O$ (50 ml), brine (50 ml), dried over $MgSO_4$, filtered, evaporated and the residue was chromatographed with 30% EtOAc-hex to provide 2.0 g (94%) of resin.

$^1$H NMR: 8.80 (d, J=2.0 Hz, 1H), 7.81 (dd, J=8.0, 2.4 Hz, 1H), 7.64 (ddd, J=15.1, 11.5, 1.1 Hz, 1H), 7.44 (dt, J=5.6, 7.9 Hz, 1H), 7.38–7.33 (m, 2H), 7.30–7.26 (m, 1H), 7.09 (ddt, J=1.0, 2.5, 8.3 Hz, 1H), 6.67 (d, J=7.6 Hz, 1H), 6.24 (t, J=11.2 Hz, 1H), 5.70–5.65 (m, 1H), 5.07–5.00 (m, 1H), 1.35 (d, J=6.4 Hz, 3H)

Step 5:

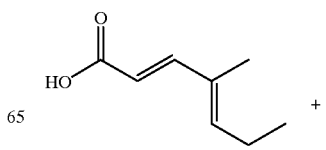

+

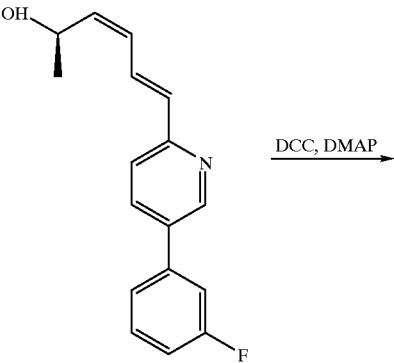

DCC, DMAP →

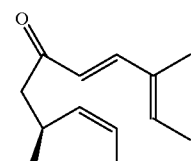

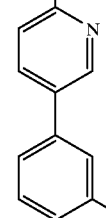

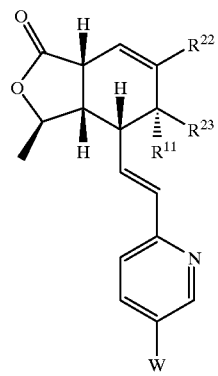

wherein $R^{11}$, $R^{22}$, $R^{23}$ and W are as defined in the table (Me is methyl, Et is ethyl, Bn is benzyl):

| Ex. | $R^{22}$ | $R^{23}$ | $R^{11}$ | W | HRMS (MH+) |
|-----|---------|---------|---------|---|------------|
| 10A | H | H | H |  | 350.1565 |
| 10B | Me | —CH₂OBn | H |  | 484.2299 |
| 10C | Me | H | —CH₂OBn |  | 484.2294 |
| 10D | Me | H | Et |  | 392.2021 |
| 10E | Me | Me | H |  | 378.1870 |
| 10F | Me | H | Me |  | 378.1870 |

To a solution of the alcohol of Step 4 (110 mg, 0.41 mmol) and the acid (85 mg, 0.61 mmol, 1.5 eq.) in CH₂Cl₂ (2 ml) was added DCC (130 mg, 0.63 mmol, 1.5 eq.) and DMAP (10 mg, 0.08 mmol, 0.2 eq.) and stirred at 0° C. until the reaction was complete. The mixture was diluted with Et₂O (50 ml), washed with aq. NaHCO₃ (2×20 ml) and brine (20 ml), dried over MgSO₄, filtered, concentrated and the residue was chromatographed with 10% EtOAc-hex to provide 135 mg (84%) of resin.

¹H NMR: 8.79 (d, J=2.4 Hz, 1H), 7.81 (dd, J=8.0, 2.4 Hz, 1H), 7.67 (ddd, J=15.3, 11.5, 1.2 Hz, 1H), 7.47–7.27 (m, 5H), 7.15 (ddt, J=2.0, 1.0, 8.3 Hz, 1H), 6.71 (d, J=15.6 Hz, 1H), 6.29 (dt, J=0.8, 11.4 Hz, 1H), 6.11–6.00 (m, 1H), 5.88 (t, J=7.6 Hz, 1H), 5.63 (t, J=10.0 Hz, 1H), 2.24–2.16 (m, 2H), 7.76 (d, J=0.8 Hz, 3H), 1.43 (d, J=6.4 Hz, 3H), 1.00 (t, J=7.6 Hz, 3H)

Step 6:

A solution of the tetraene of Step 5 (130 mg) in toluene (10 ml) was stirred in a sealed tube at 185° C. for 7 h, cooled to rt and stirred with 10 μL of DBU for 3 hr. The solution was concentrated and purified by preparative chromatography to afford 63 mg (49%) of resin.

¹H NMR: 8.72 (d, J=2.0 Hz, 1H), 7.77 (dd, J=8.4, 2.4 Hz, 1H), 7.41 (dt, J=6.0, 8.0 Hz, 1H), 7.36–7.31 (m, 2H), 7.26–7.22 (m, 1H), 7.06 (ddt, J=1.0, 2.7, 8.3 Hz, 1H), 6.66 (d, J=16.0 Hz, 1H), 6.47 (dd, J=15.8, 9.8 Hz, 1H), 5.62–561 (m, 1H), 4.55 (dq, J=4.0, 6.4 Hz, 1H), 3.27–3.24 (m, 1H), 2.80–2.75 (m, 1H), 2.56–2.52 (m, 1H), 2.02–1.97 (m, 1H), 1.78 (d, J=1.5 Hz, 3H), 1.69–1.59 (m, 1H), 1.50–1.45 (m, 1H), 1.41 (d, J=6.4 Hz, 3H), 0.92 (t, J=7.4 Hz, 3H)

Using a similar procedure, compounds of the following structure were prepared

-continued

| Ex. | $R^{22}$ | $R^{23}$ | $R^{11}$ | W | HRMS (MH$^+$) |
|---|---|---|---|---|---|
| 10G | Me | H | H | 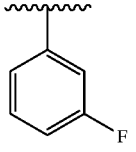 | 364.1714 |
| 10H | Me | —CH$_2$OH | H | 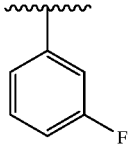 | 394.1821 |

EXAMPLE 11

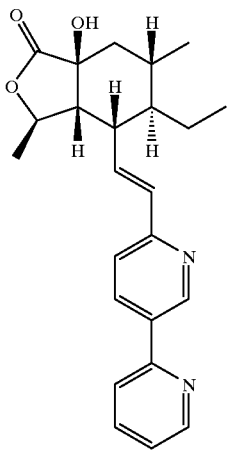

A solution of Preparation 4 (100 mg), 2(tri-n-butylstannyl)pyridine (292 mg) and Pd(PPh$_3$)$_4$ (31 mg) in toluene (5 ml) in a sealed tube was bubbled with N$_2$ and heated at 120° C. overnight. The mixture was diluted with aq. NH$_4$Cl, extracted with EtOAc, dried over MgSO$_4$, filtered, concentrated and the residue was chromatographed with 2% CH$_3$OH—CH$_2$Cl$_2$ to provide 83 mg of resin.

The resin was dissolved in THF (5ml), cooled to −78° C., a solution of 1M LHMDS in THF (290 μl) was added, stirred at 0° C. for 1 h, then cooled to −78° C. To this was added a solution of (1S)-(+)-(10-camphorsulfonyl)oxaziridine (76 mg) in THF. After stirring for about 1.5 h, it was quenched by the addition of aq. NH$_4$Cl and extracted with EtOAc. The organic layer was washed with brine, dried over MgSO$_4$, filtered, concentrated and the residue purified by preparative TLC to afford 20 mg of the title compound. HRMS: 393.2185 (MH$^+$), calculated 393.2178.

Using a similar procedure, the following compounds are also prepared:

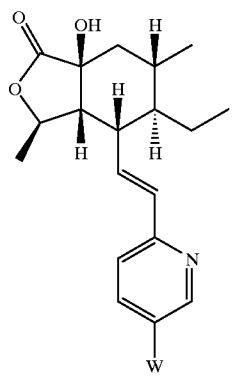

wherein W is as defined in the table:

| Ex. | W | HRMS (MH$^+$) |
|---|---|---|
| 11A | 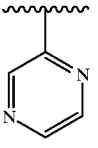 | 394.2127 |
| 11B | 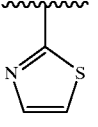 | 399.1750 |

EXAMPLE 12

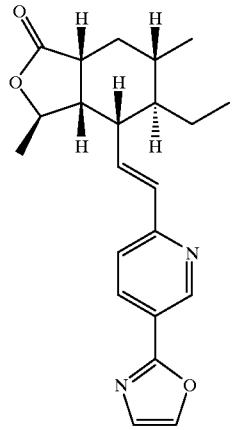

Step 1: To a solution of oxazole (75 μl, 1.1 mmol) in THF (2 ml) at −78° C. was added a solution of 2.5 M BuLi in hexanes (465 μl, 1.2 mmol, 2.2 eq.) and the mixture was stirred for 30 min. To this was added 0.5 M ZnCl$_2$ in Et$_2$O (4.3 ml, 2.2 mmol, 4 eq.) and the mixture stirred for 30 min at −78° C. and 30 min. at 0° C.

Step 2: Separately, to a suspension of Pd(PPh$_3$)$_2$Cl$_2$ (37 mg, 0.05 mmol) in THF at 0° C. was added 2.5 M BuLi in hexanes (43 μl, 0.11 mmol) and the suspension was stirred for 20 min. This solution was added to zincate of Step 1, followed by the product of Preparation 4 (200 mg, 0.5 mmol) and the mixture was refluxed overnight. It was cooled, diluted with aq. NH$_4$Cl (60 ml) and extracted with EtOAc (3×20 ml). The combined organic layer was washed with brine (20 ml), dried over MgSO$_4$, filtered, evaporated and purified by preparative TLC to provide 29 mg of resin. HRMS: 367.2025 (MH$^+$), calculated 367.2022

EXAMPLE 13

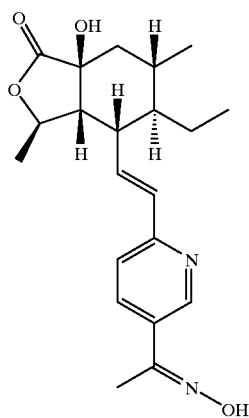

Step 1: A solution of Preparation 5 (60 mg, 0.15 mmol), Et$_3$N (26 μl, 0.19 mmol, 1.2 eq.), bis(diphenylphosphino)propane (3 mg, 7 μmol, 5 mol %), Pd(OAc)$_2$ (1.7 mg, 7.6 μl mol, 5 mol %) and vinyl n-propyl ether (85 μl, 0.76 mmol, 5 eq.) in DMF (1.5 ml) in a sealed tube was heated at 100° C. for 2 h, cooled to rt and stirred with 2N HCl (2 ml) for 2 h. The mixture was diluted with aq. NaHCO$_3$, extracted with EtOAc, dried over MgSO$_4$, filtered, concentrated and the residue was purified by preparative TLC to provide 25 mg of ketone.

Step 2: A solution of the product of Step 1 (13 mg, 36 μmol) and hydroxylamine hydrochloride (8 mg, 0.12 mmol) in pyridine (0.5 ml) was stirred overnight at rt. The mixture was diluted with aq. NH$_4$Cl (30 ml) and extracted with EtOAc (2×10 ml), the combined organic layer was washed with brine (10 ml), dried over MgSO$_4$, filtered, concentrated and the residue was purified by preparative TLC to provide 13 mg of the title compound as a resin. HRMS: 373.2113 (MH$^+$), calculated 373.2127.

Using a similar procedure the following compound is prepared:

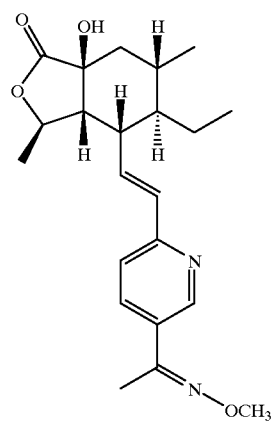

Ex. 13–2: HRMS: 387.2300 (MH$^+$)

EXAMPLE 14

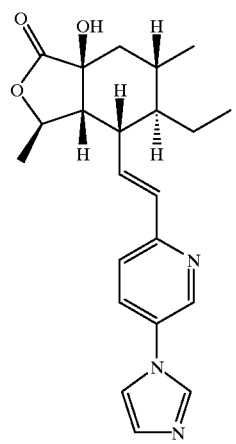

A mixture of Preparation 5 (100 mg, 0.25 mmol), imidazole (35 mg, 0.51 mmol, 2.0 eq.), copper(I) trifluoromethanesulfonate benzene complex (13 mg, 0.026 mmol, 0.1 eq.), 1,10-phenanthroline (46 mg, 0.26 mmol, 1 eq.), dibenzylideneacetone (6 mg, 0.026 mmol, 0.1 eq.) and Cs$_2$CO$_3$ (125 mg, 0.38 mmol, 1.5 eq.) in m-xylene (3 ml) in a sealed tube was bubbled with argon and heated at 13° C. overnight. The mixture was cooled to rt, diluted with aq. NH$_4$Cl (40 ml) and extracted with CH$_2$Cl$_2$ (3×10 ml). The combined organic layer was washed with brine (10 ml), dried over MgSO$_4$, filtered, concentrated and the residue was purified by preparative TLC to provide 43 mg (44%) of the title compound. HRMS: 382.2133 (MH$^+$), calculated 382.2131

Using a similar procedure, the following compound was prepared:

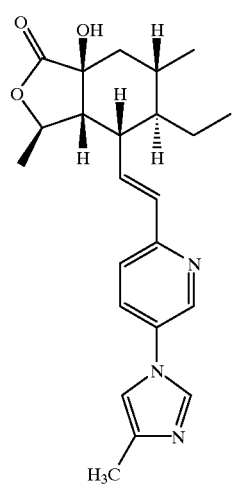

Ex. 14-2: HRMS: 396.2286 (MH$^+$)

EXAMPLE 15

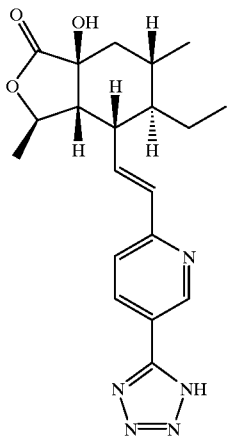

A mixture of Preparation 5 (1.0 g, 2.54 mmol), Zn(CN)$_2$ (300 mg, 2.56 mmol, 1 eq.), Pd$_2$(dba)$_3$ (116 mg, 0.13 mmol, 5 mol %) and diphenylphosphinoferrocine (170 mg, 0.31 mmol, 12 mol %) in DMF (10 ml) and H$_2$O (100 µl, 1 vol %) in a sealed tube was bubbled with argon and heated at 120° C. for 5 h. The mixture was cooled to rt, diluted with EtOAc (150 ml) and washed with H$_2$O (3×50 ml), brine (50 ml), dried over MgSO$_4$, filtered, evaporated and the crude product was chromatographed with 30% EtOAc-hex to provide 800 mg (93%) of arylcyanide.

A mixture of the arylcyanide (100 mg, 0.29 mmol), NaN$_3$ (115 mg, 1.77 mmol, 6 eq.) and NH$_4$Cl (95 mg, 1.78 mmol, 6 eq.) in DMF (2 ml) in a sealed tube was heated overnight at 120° C. It was cooled to rt, diluted with H$_2$O (10 ml), extracted with CH$_2$Cl$_2$, concentrated and the crude product was purified by preparative TLC to give 50 mg of the title compound as a solid. HRMS: 384.2033 (MH$^+$), calculated 384.2036.

EXAMPLE 16

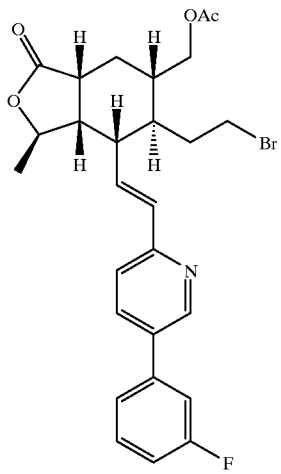

16A

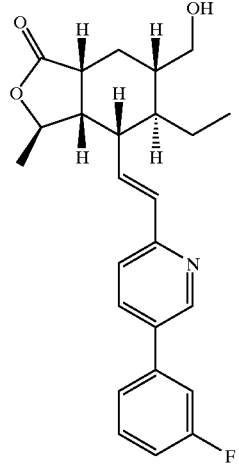

16B

Step 1:

To a solution of compound 31a (wherein W is 3-fluorophenyl) (480 mg, 1.2 mmol) in CH$_2$Cl$_2$ was added 1M solution of BBr$_3$ in CH$_2$Cl$_2$ (11.7 ml, 11.7 mmol, 10 eq.), and the mixture refluxed for 2.5 h, then diluted with aq. NaHCO$_3$ (100 ml). After stirring for about 30 min. the organic layer was isolated and the aqueous layer was extracted with CH$_2$Cl$_2$ (2×40 ml). The combined organic layer was washed with aq. NaHCO$_3$ (100 ml), brine (100 ml), dried over MgSO$_4$, filtered and evaporated to give the crude alcohol.

The crude alcohol was dissolved in CH$_2$Cl$_2$ (12 ml), cooled to 0° C., and Ac$_2$O (225 µL, 2.4 mmol, 2 eq.) was added followed by DMAP (27 mg, 0.24 mmol, 0.2 eq.) and Et$_3$N (0.5 ml, 3.6 mmol, 3 eq.). After stirring for about 2 h, the mixture was diluted with EtOAc (80 ml), washed with aq. NaHCO$_3$ (2×50 ml), and brine. The solution was dried over MgSO$_4$, filtered, evaporated and the residue was chromatographed with 40% EtOAc-hex to provide 350 mg (56%) of Example 16-A as a white foam. HRMS: 530.1336, calculated 530.1342.

Step 2:

A mixture of Example 16-A (53 mg, 0.1 eq.), NaCNBH$_3$ (32 mg, 0.5 mmol, 5 eq.) in HMPA (1 ml) was stirred at 80° C. for 4 h, cooled to rt, diluted with H$_2$O (30 ml) and extracted with EtOAc (3×15 ml). The combined organic layer was washed with brine (20 ml), dried over MgSO$_4$, filtered, concentrated and purified by preparative TLC to provide 27 mg of resin. To this was added K$_2$CO$_3$ (32 mg) in CH$_3$OH—H$_2$O mixture (2 ml of 9:1 v/v) and the solution was stirred at rt for 1 h. The mixture was diluted with H$_2$O (30 ml), extracted with EtOAc (3×10 ml), and the combined organic layers were washed with brine (10 ml), dried over MgSO$_4$, filtered, concentrated and filtered through a short SiO$_2$ plug to provide 17 mg (72%) of Example 16-B as a resin. HRMS: 410.2126, calculated 410.2131

Using a similar procedure, the compounds with the following structure were prepared

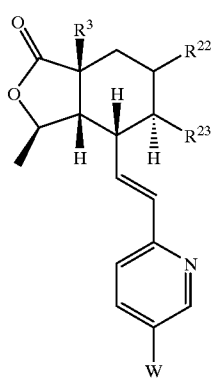

wherein $R^3$, $R^{22}$, $R^{23}$ and W are as defined in the table (Me is methyl, Et is ethyl):

| Ex. | $R^3$ | $R^{22}$ | $R^{23}$ | W | HRMS (MH+) |
|---|---|---|---|---|---|
| 16C | H | —CH$_2$OH | Et | 2-F-phenyl | 410.2138 |
| 16D | H | —CH=N—OH | Et | 2-F-phenyl | 423.2090 |
| 16E | H | —CH=N—OMe | Et | 2-F-phenyl | 437.2235 |
| 16F | H | —CH=N—OEt | Et | 2-F-phenyl | 451.2396 |
| 16G | OH | —CH$_2$OH | Et | 2-F-phenyl | 426.2075 |

The following formulations exemplify some of the dosage forms of this invention. In each, the term "active compound" designates a compound of formula I.

Example A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|  | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

The activity of the compounds of formula I can be determined by the following procedures.

In Vitro Testing Procedure for Thrombin Receptor Antagonists: Preparation of [$^3$H]haTRAP A(pF-F)R(ChA)(hR)(I$_2$—Y)—NH$_2$ (1.03 mg) and 10% Pd/C (5.07 mg) were suspended in DMF (250 μl) and diisopropylethylamine (10 μl). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of Platelet Membranes

Platelet membranes were prepared using a modification of the method of Natarajan et al (Natarajan et al, *Int. J. Peptide Protein Res.* 45:145–151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were resuspended in 10 mM Tris-HCl, pH 7.5, 150 mM NaCl, 5 mM EDTA, to a total volume of 200 ml and centrifuged at 4400×g for 10 minutes. This step was repeated two additional times. Platelets were resuspended in 5 mM Tris-HCl, pH 7.5, 5 mM EDTA to a final volume of approximately 30 ml and were homogenized with 20 strokes in a Dounce homogenizer. Membranes were pelleted at 41,000×g, resuspended in 40–50 ml 20 mM Tris-HCl, pH 7.5, 1 mM EDTA, 0.1 mM dithiothreitol, and 10 ml aliquots were frozen in liquid $N_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and resuspended in 20–25 ml 50 mM Tris-HCl, pH 7.5, 10 mM $MgCl_2$, 1 mM EGTA, and 1% DMSO. Aliquots of membranes were frozen in liquid $N_2$ and stored at −80° C. Membranes were stable for at least 3 months. 20 units of platelet concentrates typically yielded 250 mg of membrane protein. Protein concentration was determined by a Lowry assay (Lowry et al, *J. Biol. Chem.*, 193:265–275 (1951)).

High Throughput Thrombin Receptor Radioligand Binding Assay

Thrombin receptor antagonists were screened using a modification of the thrombin receptor radioligand binding assay of Ahn et al. (Ahn et al, *Mol. Pharmacol.*, 51:350–356 (1997)). The assay was performed in 96 well Nunc plates (Cat. No. 269620) at a final assay volume of 200 μl. Platelet membranes and [$^3$H]haTRAP were diluted to 0.4 mg/ml and 22.2 nM, respectively, in binding buffer (50 mM Tris-HCl, pH 7.5, 10 mM $MgCl_2$, 1 mM EGTA, 0.1% BSA). Stock solutions (10 mM in 100% DMSO) of test compounds were further diluted in 100% DMSO. Unless otherwise indicated, 10 μl of diluted compound solutions and 90 μl of radioligand (a final concentration of 10 nM in 5% DMSO) were added to each well, and the reaction was started by the addition of 100 μl of membranes (40 μg protein/well). The binding was not significantly inhibited by 5% DMSO. Compounds were tested at three concentrations (0.1, 1 and 10 μM). The plates were covered and vortex-mixed gently on a Lab-Line Titer Plate Shaker for 1 hour at room temperature. Packard UniFilter GF/C filter plates were soaked for at least 1 hour in 0.1% polyethyleneimine. The incubated membranes were harvested using a Packard FilterMate Universal Harvester and were rapidly washed four times with 300 μl ice cold 50 mM Tris-HCl, pH 7.5, 10 mM $MgCl_2$, 1 mM EGTA. MicroScint 20 scintillation cocktail (25 μl) was added to each well, and the plates were counted in a Packard Top-Count Microplate Scintillation Counter. The specific binding was defined as the total binding minus the nonspecific binding observed in the presence of excess (50 μM) unlabeled haTRAP. The % inhibition by a compound of [$^3$H] haTRAP binding to thrombin receptors was calculated from the following relationship:

% Inhibition=Total binding-Binding in the presence of a test compound×100 Total binding-Nonspecific binding Materials A(pF-F)R(ChA)(hR)Y—$NH_2$ and A(pF-F)R(ChA)(hR)($I_2$—Y)—$NH_2$, were custom synthesized by AnaSpec Inc. (San Jose, Calif.). The purity of these peptides was >95%. Tritium gas (97%) was purchased from EG&G Mound, Miamisburg Ohio. The gas was subsequently loaded and stored on an IN/US Systems Inc. Trisorber. MicroScint 20 scintillation cocktail was obtained from Packard Instrument Co.

Protocol for Ex-Vivo Platelet Aggregation in Cynomolgus Whole Blood Drug Administration and Blood Collection:

Conscious chaired cynomolgus monkeys are allowed to equilibrate for 30 min. A needle catheter is inserted into a brachial vein for infusion of test drugs. Another needle catheter is inserted into the other brachial or saphenous vein and used for blood sampling. In those experiments where the compound is administered orally only one catheter is used. A baseline blood sample (1–2 ml) is collected in vacutainer tubes containing a thrombin inhibitor CVS 2139 (100 μg/0.1 ml saline) as an anticoaculant. The drug is then infused intravenously over a period of 30 min. Blood samples (1 ml) are collected at 5, 10, 20, 30 min during and 30, 60, 90 min after termination of the drug infusion. In PO experiments the animals are dosed with the drug using a gavage cannula. Blood samples are collected at 0, 30, 60, 90, 120,180, 240, 300, 360 min after dosing. 0.5 ml of the blood is used for whole blood aggregation and the other 0.5 ml is used for determining the plasma concentration of the drug or its metabolites. Aggregation is performed immediately after collection of the blood sample as described below.

Whole Blood Aggregation:

A 0.5 ml blood sample is added to 0.5 ml of saline and warmed to 37° C. in a Chronolog whole blood aggregometer. Simultaneously, the impedance electrode is warmed in saline to 37° C. The blood sample with a stir bar is place in the heating block well, the impedance electrode is placed in the blood sample and the collection software is started. The software is allowed to run until the baseline is stabilized and then a 20 Ω calibration check is performed. 20 Ω is equal to 4 blocks on the graphic produced by the computer software. The agonist (haTRAP) is added by an adjustable volume pipette (5–25 μl) and the aggregation curve is recorded for 10 minutes. Maximum aggregation in 6 minutes following agonist is the value recorded.

In vitro Platelet Aggregation Procedure:

Platelet aggregation studies were performed according to the method of Bednar et al. (Bednar, B., Condra, C., Gould, R. J., and Connolly, T. M., *Throm. Res.*, 77:453–463 (1995)). Blood was obtained from healthy human subjects who were aspirin free for at least 7 days by venipuncture using ACD as anticoagulant. Platelet rich plasma was prepared by centrifugation at 100×g for 15 minutes at 15 deg C. Platelets were pelleted at 3000×g and washed twice in buffered saline containing 1 mM EGTA and 20 μg/ml apyrase to inhibit aggregation. Aggregation was performed at room temperature in buffered saline supplemented with 0.2 mg/ml human fibrinogen. Test compound and platelets were preincubated in 96-well flat-bottom plates for 60 minutes. Aggregation was initiated by adding 0.3 μM haTRAP or 0.1 U/ml thrombin and rapidly vortexing the mixture using a Lab Line Titer Plate Shaker (speed 7). Percent aggregation was monitored as increasing light transmittance at 405 nm in a Spectromax Plate Reader.

In vivo Antitumor Procedure:

Tests in the human breast carcinoma model in nude mouse are conducted according to the procedure reported in S. Even-Ram et. al., *Nature Medicine*, 4, 8 (1988), p. 909–914.

Cannabinoid CB2 Receptor Binding Assay

Binding to the human cannabinoid CB2 receptor was carried out using the procedure of Showalter, et al (1996, *J. Pharmacol Exp Ther.* 278(3), 989–99), with minor modifications. All assays were carried out in a final volume of 100 ul. Test compounds were resuspended to 10 mM in DMSO, then serially diluted in 50 mM Tris, pH 7.1, 3 mM $MgCl_2$, 1 mM EDTA, 50% DMSO. Aliquots (10 ul) of each diluted sample were then transferred into individual wells of a 96-well microtiter plate. Membranes from human CB2 transfected CHO/Ki cells (Receptor Biology, Inc) were resuspended in binding buffer (50 mM Tris, pH 7.1, 3 mM MgCl2, 1 mM EDTA, 0.1% fatty acid free bovine serum albumin), then added to the binding reaction (~15 ug in 50 ul per assay). The reactions were initiated with the addition of [$^3$H] CP-55,940 diluted in binding buffer (specific activity=180 Ci/mmol; New England Nuclear, Boston, Mass.). The final ligand concentration in the binding reaction was 0.48 nM. Following incubation at room temperature for 2 hours, membranes were harvested by filtration through pretreated (0.5% polyethylenimine; Sigma P-3143) GF-C filter plates (Unifilter-96, Packard) using a TomTec Mach 3U 96-well cell harvester (Hamden, Conn.). Plates were washed 10 times in 100 ul binding buffer, and the membranes allowed to air dry. Radioactivity on membranes was quantitated following addition of Packard Omniscint 20 scintillation fluid using a TopCount NXT Microplate Scintillation and Luminescence Counter (Packard, Meriden, Conn.). Non-linear regression analysis was performed using Prism 20b. (GraphPad Software, San Diego, Calif.).

Using the test procedures described above, representative compounds of formula I were found to have thrombin receptor $IC_{50}$ values (i.e., the concentration at which a 50% inhibition of thrombin receptor was observed) of 1 to 1000 nM, preferably 1–100 nM, more preferably 1–20 nM. CB2 Ki values range from 1 to 1000 nM, preferably 1–200 nM, more preferably 1–100 nM.

We claim:

1. A compound represented by the structural formula

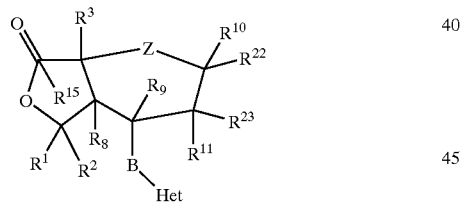

or a pharmaceutically acceptable salt thereof, wherein:

Z is —$CH_2$—;

$R^1$ is H, $C_1$–$C_6$ alkyl, fluoro($C_1$–$C_6$)alkyl, difluoro ($C_1$–$C_6$)alkyl, trifluoro-($C_1$–$C_6$)alkyl, $C_3$–$C_7$ cycloalkyl, $C_2$–$C_6$ alkenyl, aryl($C_1$–$C_6$)alkyl, aryl ($C_2$–$C_6$)alkenyl, hydroxy-($C_1$–$C_6$)alkyl, ($C_1$–$C_6$) alkoxy($C_1$–$C_6$)alkyl, amino-($C_1$–$C_6$)alkyl, aryl or thio($C_1$–$C_6$)alkyl;

$R^2$ is H;

$R^3$ is H, hydroxy, $C_1$–$C_6$ alkoxy, —$NR^{18}R^{19}$, —$SOR^{16}$, —$SO_2R^{17}$, —C(O)$OR^{17}$, —C(O)$NR18R^{19}$, $C_1$–$C_6$ alkyl, halogen, fluoro($C_1$–$C_6$)alkyl, difluoro($C_1$–$C_6$) alkyl, trifluoro($C_1$–$C_6$)alkyl, $C_3$–$C_7$ cycloalkyl, $C_2$–$C_6$ alkenyl, aryl($C_1$–$C_6$)alkyl, aryl($C_2$–$C_6$) alkenyl, hydroxy($C_1$–$C_6$)alkyl, amino($C_1$–$C_6$)alkyl, aryl, thio($C_1$–$C_6$)alkyl, ($C_1$–$C_6$)alkoxy($C_1$–$C_6$)alkyl or ($C_1$–$C_6$)alkylamino($C_1$–$C_6$)alkyl;

Het is pyridyl, wherein the ring nitrogen can form an N-oxide or a quaternary group with a $C_1$–$C_4$ alkyl group, wherein Het is attached to B by a carbon atom ring member, and wherein the Het group is substituted by 1 to 4 substituents of W, wherein W is independently selected from the group consisting of H; $C_1$–$C_6$ alkyl; fluoro($C_1$–$C_6$)alkyl; difluoro ($C_1$–$C_6$)alkyl; trifluoro-($C_1$–$C_6$)-alkyl; $C_3$–$C_7$ cycloalkyl; $C_2$–$C_6$ alkenyl; $R^{21}$-aryl($C_1$–$C_6$)alkyl; $R^{21}$-aryl-($C_1$–$C_6$)-alkenyl; $R^{21}$-aryloxy; $R^{21}$-aryl-NH—; hydroxy($C_1$–$C_6$)alkyl; dihydroxy($C_1$–$C_6$) alkyl; amino($C_1$–$C_6$)alkyl; ($C_1$–$C_6$)alkylamino-($C_1$–$C_6$)alkyl; di-(($C_1$–$C_6$)alkyl)-amino-($C_1$–$C_6$) alkyl; thio($C_1$–$C_6$)alkyl; $C_1$–$C_6$ alkoxy; $C_2$–$C_6$ alkenyloxy; halogen; —$NR^4R^5$; —CN; —OH; —$COOR^{17}$; —$COR^{16}$; —$OSO_2CF_3$; —$CH_2OCH_2CF_3$; ($C_1$–$C_6$)alkylthio; —C(O)$NR^4R^5$; —$OCHR^8$-phenyl; phenoxy-($C_1$–$C_6$)alkyl; —$NHCOR^{16}$; —$NHSO_2R^{16}$; biphenyl; —OC($R^6$)$_2$ $COOR^7$; —OC($R^6$)$_2$C(O)$NR^4R^5$; ($C_1$–$C_6$)alkoxy: —C(=$NOR^{17}$)$R^{18}$;

$C_1$–$C_6$ alkoxy substituted by ($C_1$–$C_6$)alkyl, amino, —OH, $COOR^{17}$, —$NHCOOR^{17}$, —$CONR^4R^5$, aryl, aryl substituted by 1 to 3 substutuents independently selected from the group consisting of halogen, —$CF_3$, $C_1$–$C_6$ alkyl, $C_1$–$C_6$ alkoxy and —$COOR^{17}$, —C(O)$NR^4R^5$; and $R^{21}$-aryl;

$R^4$ and $R^5$ are independently selected from the group consisting of H, $C_1$–$C_6$ alkyl, phenyl, benzyl and $C_3$–$C_7$ cycloalky;

$R^6$ is independently selected from the group consisting of H, $C_1$–$C_6$ alkyl, phenyl, ($C_3$–$C_7$)cycloalkyl, ($C_3$–$C_7$)cycloalkyl($C_1$–$C_6$)alkyl, ($C_1$–$C_6$)alkoxy ($C_1$–$C_6$)alkyl, hydroxy($C_1$–$C_6$)alkyl and amino ($C_1$–$C_6$)alkyl;

$R^7$ is H or ($C_1$–$C_6$)alkyl;

$R^8$, $R^{10}$ and $R^{11}$ are each H;

$R^9$ is H, OH, $C_1$–$C_6$ alkoxy, halogen or halo($C_1$–$C_6$) alkyl;

B is —CH=CH—;

$R^{16}$ is $C_1$–$C_6$ lower alkyl, phenyl or benzyl;

$R^{17}$, $R^{18}$ and $R^{19}$ are independently selected from the group consisting of H, $C_1$–$C_6$ alkyl, phenyl, benzyl;

$R^{21}$ is 1 to 3 substutuents independently selected from the group consisting of hydrogen, CN, —$CF3$, —$OCF_3$, halogen, —$NO_2$, $C_1$–$C_6$ alkyl, $C_1$–$C_6$alkoxy, ($C_1$–$C_6$)alkylamino, di-(($C_1$–$C_6$)alkyl) amino, amino($C_1$–$C_6$)alkyl, ($C_1$–$C_6$)-alkylamino ($C_1$–$C_6$)alkyl, di-(($C_1$–$C_6$)alkyl)-amino($C_1$–$C_6$) alkyl, hydroxy-($C_1$–$C_6$)alkyl, —$COOR^{17}$, —$COR^{17}$, —$NHCOR^{16}$, —$NHSO_2R^{16}$, —$NHSO_2CH_2CF_3$, or —C(=$NOR^{17}$)$R^{18}$;

$R^{22}$ and $R^{23}$ are independently selected from the group consisting of hydrogen, $R^{24}$—($C_1$–$C_{10}$)alkyl, $R_{24}$-($C_2$–$C_{10}$)alkenyl, $R^{24}$—($C_2$–$C_{10}$)alkynyl, —$R^{25}$-aryl, $R^{25}$-aryl($C_1$–$C_6$)alkyl, $R^{29}$—($C_3$–$C_7$) cycloalkyl, $R^{29}$—($C_3$–$C_7$)cyclo-alkenyl, —OH, —OC(O)$R^{30}$, —C(O)$OR^{30}$, —C(O)$R^{30}$, —C(O) $NR^{30}R^{31}$, —$NR^{30}R^{31}$, —$NR^{30}$C(O)$R^{31}$, —$NR^{30}$C (O)$NR^{31}R^{32}$, —$NHSO_2R^{30}$, —OC(O)$NR^{30}R^{31}$, $R^{24}$—($C_1$–$C_{10}$)alkoxy, $R^{24}$—($C_2$–$C_{10}$)-alkenyloxy, $R^{24}$—($C_2$–$C_{10}$)alkynyloxy, $R^{29}$—($C_3$–$C_7$) cycloalkyloxy, $R^{29}$—($C_3$–$C_7$)cyclo-alkenyloxy, $R^{29}$—($C_3$–$C_7$)cycloalkyl-NH—, —$NHSO_2NHR^{16}$ and —CH(=$NOR^{17}$);

or $R^{22}$ and $R^{10}$ together with the carbon to which they are attached, or $R^{23}$ and $R^{11}$ together with the carbon to which they are attached, independently form a $R^{42}$-substituted carbocyclic ring of 3–10 atoms;

$R^{24}$ is 1, 2 or 3 substituents independently selected from the group consisting of hydrogen, halogen, —OH, $(C_1-C_6)$alkoxy, $R^{35}$-aryl, $(C_1-C_{10})$-alkyl-C(O)—, $(C_2-C_{10})$-alkenyl-C(O)—, $(C_2-C_{10})$alkynyl-C(O)—, $R^{26}$—$(C_3-C_7)$cycloalkyl, $R^{26}$—$(C_3-C_7)$cycloalkenyl, —OC(O)$R^{30}$, —C(O)O$R^{30}$, —C(O)$R^{30}$, —C(O)N$R^{30}R^{31}$, —N$R^{30}R^{31}$, —N$R^{30}$C(O)$R^{31}$, —N$R^{30}$C(O)N$R^{31}R^{32}$, —NHSO$_2R^{30}$, —OC(O)N$R^{30}R^{31}$, $R^{29}$—$(C_3-C_7)$-cycloalkyloxy, $R^{29}$—$(C_3-C_7)$cyclo-alkenyloxy, $R^{29}$—$(C_3-C_7)$cycloalkyl-NH—, —NHSO$_2$NH$R^{16}$ and —CH(=NO$R^{17}$);

$R^{25}$ is , 2 or 3 substituents independently selected from the group consisting of hydrogen. halogen, —COO$R^{36}$, —CN, —C(O)N$R^{37}R^{38}$, —N$R^{39}$C(O)$R^{40}$, —O$R^{36}$, $(C_3-C_7)$cycloalkyl, $(C_3-C_7)$cycloalkyl-$C_1-C_6$)alkyl, $(C_1-C_6)$alkyl$(C_3-C_7)$cycloalkyl-$(C_1-C_6)$alkyl, halo$(C_1-C_6)$alkyl$(C_3-C_7)$cycloalkyl$(C_1-C_6)$alkyl, hydroxy$(C_1-C_6)$alkyl, and $(C_1-C_6)$alkoxy$(C_1-C_6)$alkyl;

$R^{26}$ is 1, 2, or 3 substituents independently selected from the group consisting of hydrogen, halogen and $(C_1-C_6)$alkoxy;

$R^{29}$ is 1, 2 or 3 substituents independently selected from the group consisting of hydrogen, $(C_1-C_6)$alkyl, —OH, $(C_1-C_6)$alkoxy and halogen;

$R^{30}$, $R^{31}$ and $R^{32}$ are independently selected from the group consisting of hydrogen, $(C_1-C_{10})$-alkyl, $(C_1-C_6)$alkoxy$(C_1-C_{10})$-alkyl, $R^{25}$-aryl$(C_1-C_6)$-alkyl, $R^{33}$—$(C_3-C_7)$cycloalkyl, $R^{34}$-$(C_3-C_7)$cycloalkyl$(C_1-C_6)$alkyl, and $R^{25}$-aryl;

$R^{33}$ is hydrogen, $(C_1-C_6)$alkyl, OH—$(C_1-C_6)$alkyl or $(C_1-C_6)$alkoxy;

$R^{35}$ is 1 to 4 substituents independently selected from the group consisting of hydrogen, $(C_1-C_6)$alkyl, —OH, halogen, —CN, $(C_1-C_6)$alkoxy, trihalo$(C_1-C_6)$alkoxy, $(C_1-C_6)$alkylamino, di($(C_1-C_6)$alkyl)amino, —OCF3, OH—$(C_1-C_6)$alkyl, —CHO, —C(O)$(C_1-C_6)$-alkylamino, —C(O)di($(C_1-C_6)$alkyl)amino, —NH$_2$, —NHC(O)$(C_1-C_6)$alkyl and —N($(C_1-C_6)$alkyl)C(O)$(C_1-C_6)$alkyl;

$R^{36}$ is hydrogen, $(C_1-C_6)$alkyl, halo$(C_1-C_6)$alkyl, dihalo$(C_1-C_6)$alkyl or trifluoro$(C_1-C_6)$alkyl, $R^{37}$ and $R^{38}$ are independently selected from the group consisting of hydrogen, $(C_1-C_6)$alkyl, aryl$(C_1-C_6)$alkyl, phenyl and $(C_3-C_{15})$cycloalkyl;

$R^{39}$ and $R^{40}$ are independently selected from the group consisting of hydrogen, $(C_1-C_6)$alkyl, aryl$(C_1-C_6)$alkyl, phenyl and $(C_3-C_{15})$-cycloalkyl; and $R^{42}$ is 1 to 3 substituents independently selected from the group consisting of hydrogen, —OH, $(C_1-C_6)$alkyl and $(C_1-C_6)$alkoxy.

2. A compound of claim 1 wherein $R^8$, $R^{10}$ and $R^{11}$ are each hydrogen, and $R^3$ is hydrogen, OH, $C_1-C_6$ alkoxy, —NH$R^{18}$ or $C_1-C_6$ alkyl.

3. A compound of claim 1 wherein $R^9$ is H, OH or $C_1-C_6$ alkoxy.

4. A compound of claim 1 wherein $R^1$ is $C_1-C_6$ alkyl.

5. A compound of claim 1 wherein W is $C_1-C_6$ alkyl, or $R^{21}$-aryl.

6. A compound of claim 1 wherein $R^{22}$ $R^{23}$ are independently selected from the group consisting of OH, $(C_1-C_{10})$ alkyl, $C_2-C_{10})$-alkenyl, $(C_2-C_{10})$alkynyl, trifluoro$(C_1-C_{10})$-alkyl, trifluoro$(C_2-C_{10})$-alkenyl, trifluoro$(C_2-C_{10})$alkynyl, $(C_3-C_7)$cycloalkyl, $R^{25}$-aryl, $R^{25}$-aryl$(C_1-C_6)$alkyl, $R^{25}$-arylhydroxy$(C_1-C_6)$alkyl, $R^{25}$-arylalkoxy$(C_1-C_6)$alkyl, $(C_3-C_7)$-cycloalkyl-$(C_1-C_6)$alkyl, $(C_1-C_{10})$alkoxy, $(C_3-C_7)$ cycloalkyloxy, $(C_1-C_6)$alkoxy$(C_1-C_6)$alkyl, OH—$(C_1-C_6)$ alkyl, and trifluoro$(C_1-C_{10})$alkoxy.

7. A compound of claim 1 wherein $R^{22}$ and $R^{23}$ are independently selected from the group consisting of $(C_1-C_{10})$alkyl and OH—$(C_1-C_{10})$alkyl.

8. A compound of claim 1 wherein $R^2$ is hydrogen; $R^3$ is hydrogen OH, $C_1-C_6$ alkoxy, —NH$R^{18}$ or $C_1-C_6$ alkyl; $R^9$ is H, OH or $C_1-C_6$ alkoxy; and $R^1$ is $C_1-C_6$ alkyl.

9. A compound of claim 8 wherein $R^{22}$ and $R^{23}$ are independently selected from the group consisting of OH, $(C_1-C_{10})$alkyl, $(C_2-C_{10})$-alkenyl, $(C_2-C_{10})$alkynyl, trifluoro$(C_1-C_{10})$-alkyl, trifluoro$(C_2-C_{10})$-alkenyl, trifluoro$(C_2-C_{10})$alkynyl, $(C_3-C_7)$cycloalkyl, $R^{25}$-aryl, $R^{25}$-aryl$(C_1-C_6)$alkyl, $R^{25}$-arylhydroxy$(C_1-C_6)$alkyl, $R^{25}$-arylalkoxy$(C_1-C_6)$alkyl, $(C_3-C_7)$-cycloalkyl-$(C_1-C_6)$alkyl, $(C_1-C_{10})$alkoxy, $(C_3-C_7)$cycloalkyloxy, $(C_1-C_6)$alkoxy $(C_1-C_6)$alkyl, OH—$(C_1-C_6)$alkyl, and trifluoro$(C_1-C_{10})$alkoxy.

10. A compound of claim 8 wherein $R^{22}$ and $R^{23}$ are independently selected from the group consisting of $(C_1-C_{10})$alkyl and OH—$(C_1-C_{10})$alkyl.

11. A compound of claim 8 wherein B is trans —CH=CH—.

12. A compound of claim 1 selected from the group consisting of compounds of the formula

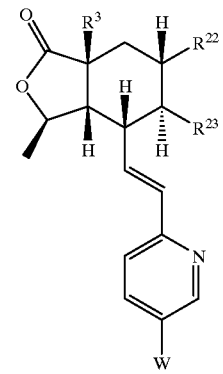

wherein $R^3$, $R^{22}$, $R^{23}$ and W are as defined in the following table (Me is methyl, Et is ethyl, Ac is acetyl and Ph is phenyl):

| $R^3$ | $R^{22}$ | $R^{23}$ | W |
|---|---|---|---|
| H | Me | Et |  |
| H | Me | Et | 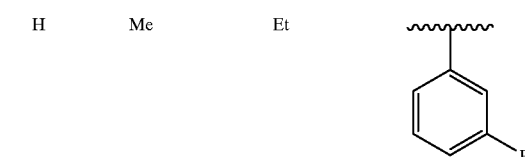 |

-continued
| R³ | R²² | R²³ | W |
|---|---|---|---|
| H | Me | Et | 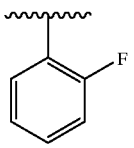 2-F phenyl |
| H | Me | Et | 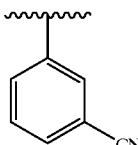 2-Cl phenyl |
| H | Me | Et | 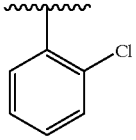 3-Cl phenyl |
| H | Me | Et | 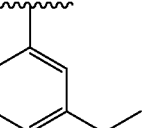 2,3-diCl phenyl |
| H | H | Ph | 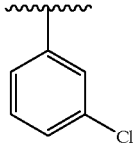 3-F phenyl |
| H | Me | Et | 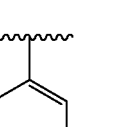 3-(NHSO₂Et) phenyl |
| OH | Me | Et | 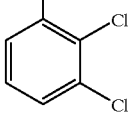 2-Me phenyl |
| OH | Me | Et | 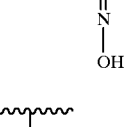 3-Me phenyl |
| OH | Me | Et | 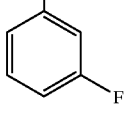 2-CN phenyl |
-continued
| R³ | R²² | R²³ | W |
|---|---|---|---|
| OH | Me | Et | 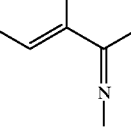 3-CN phenyl |
| OH | Me | Et | 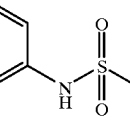 3-acetyl phenyl |
| OH | Me | Et | 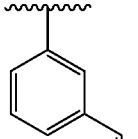 3-(C(=NOH)Me) phenyl |
| OH | Me | Et |  3-(C(=NOMe)Me) phenyl |
| OH | Me | Et |  3-(CH=NOH) phenyl |
| OH | Me | Et | 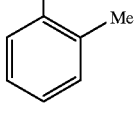 3-(CH=NOMe) phenyl |
| OH | Me | Et | 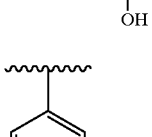 2-(CH=NOH) phenyl |

-continued

| R³ | R²² | R²³ | W |
|---|---|---|---|
| OH | Me | Et | 2-(CH=N-OMe)-phenyl |
| OH | Me | Et | 3-(CH₂OH)-phenyl |
| OH | Me | Et | 2-(CH₂OH)-phenyl |
| H | H | Et | 2-F-phenyl |
| H | Ph | Me | 3-F-phenyl |
| H | Ph | Me | 3-Cl-phenyl |
| OH | Me | Et | 2-(CH=N-OEt)-phenyl |
| OH | Me | Et | phenyl |
| OH | Me | Et | 3-isopropyl-phenyl |

-continued

| R³ | R²² | R²³ | W |
|---|---|---|---|
| OMe | Me | Et | 2-(CH₂OH)-phenyl |
| OH | Me | Et | 3-(CH(OH)Me)-phenyl |
| OH | Me | Et | 2-(C(=O)Me)-phenyl |
| OH | Me | Et | 2-(CH(OH)Me)-phenyl |
| OH | H | Et | 2-Me-phenyl |
| OH | H | Et | 3-F-phenyl |
| OH | Me | Et | 4-OH-phenyl |
| OH | Me | Et | 5-Cl-2-OMe-phenyl |

-continued

| R³ | R²² | R²³ | W |
|---|---|---|---|
| OH | H | Me | 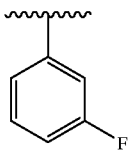 3-F phenyl |
| OH | H | Me | 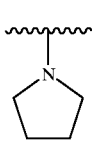 3-CN phenyl |
| OH | Me | Et | 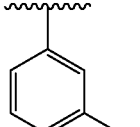 4-F, 2-OMe phenyl |
| OH | H | Me | 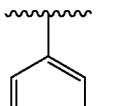 2-Me phenyl |
| OH | H | Me | 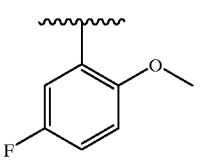 phenyl |
| OH | Me | Et | 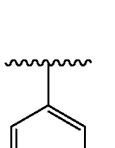 2-C(Me)=N-OH phenyl |
| OH | Me | Et | 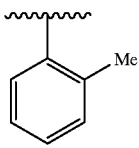 2-C(Me)=N-OMe phenyl |
| OH | Me | Et |  2-C(Me)=N-OEt phenyl |
| OH | Me | Et | 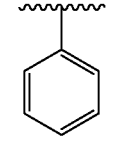 3-C(Me)₂OH phenyl |

-continued

| R³ | R²² | R²³ | W |
|---|---|---|---|
| OH | Me | Et | 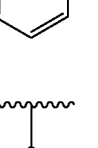 N-pyrrolidinyl |
| H | —CH₂—OAc | —(CH₂)₂—Br | 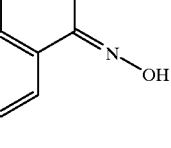 3-F phenyl |
| H | —CH₂—OH | Et | 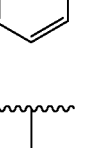 3-F phenyl |
| H | —CH₂—OH | Et | 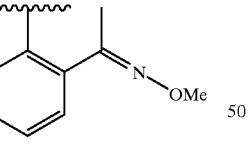 2-F phenyl |
| H | —CH=N—OH | Et | 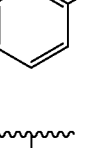 2-F phenyl |
| H | —CH=N—OMe | Et | 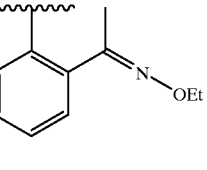 2-F phenyl |
| OH | —CH₂—OH | Et | 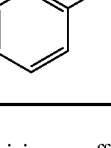 2-F phenyl |

13. A pharmaceutical composition comprising an effective amount of a compound of claim 1 and a pharmaceutically acceptable carrier.

14. A method of inhibiting thrombin receptors comprising administering to a mammal in need of such treatment an effective amount of a compound of claim 1.

* * * * *